United States Patent [19]

Matsura et al.

[11] Patent Number: 4,979,497

[45] Date of Patent: Dec. 25, 1990

[54] ENDOSCOPE

[75] Inventors: Nobuyuki Matsuura, Hino; Jun Hiroya, Tokyo, both of Japan

[73] Assignee: Olympus Optical Co., Ltd., Tokyo, Japan

[21] Appl. No.: 498,127

[22] Filed: Mar. 23, 1990

[30] Foreign Application Priority Data

| Jun. 6, 1989 | [JP] | Japan | 1-144635 |
| Jun. 7, 1989 | [JP] | Japan | 1-144835 |
| Jun. 7, 1989 | [JP] | Japan | 1-144836 |
| Jun. 7, 1989 | [JP] | Japan | 1-66608[U] |
| Jun. 13, 1989 | [JP] | Japan | 1-69500[U] |
| Sep. 22, 1989 | [JP] | Japan | 1-247492 |

[51] Int. Cl.$^5$ .................................................. A61B 1/04
[52] U.S. Cl. .................................... 128/4; 128/6; 358/98
[58] Field of Search .................. 128/4, 4 A, 6; 358/98

[56] References Cited

U.S. PATENT DOCUMENTS

| 4,625,714 | 12/1986 | Toyota et al. | 128/6 |
| 4,825,850 | 5/1989 | Opie et al. | 128/4 |
| 4,841,952 | 6/1989 | Sato et al. | 128/6 |
| 4,901,142 | 2/1990 | Ikund et al. | 128/4 X |

FOREIGN PATENT DOCUMENTS

| 58-182704 | 12/1983 | Japan . |
| 61-50478 | 3/1986 | Japan . |
| 63-186619 | 8/1988 | Japan . |
| 63-197430 | 8/1988 | Japan . |
| 63-220832 | 9/1988 | Japan . |
| 63-220833 | 9/1988 | Japan . |
| 64-83242 | 3/1989 | Japan . |
| 64-80102 | 5/1989 | Japan . |

Primary Examiner—William H. Grieb
Attorney, Agent, or Firm—Armstrong, Nikaido, Marmelstein, Kubovcik & Murray

[57] ABSTRACT

The endoscope comprises an elongate insertable part including an observing window in the tip part and a sucking tube path in the interior, an image forming optical system receiving a light from an object coming in from the observing window and forming an endoscope image, an imaging apparatus for imaging the endoscope image formed by the image forming optical system and an operating part connected to the insertable part at the base on the side opposite the tip part. The operating part includes a holding part arranged on the side near to the insertable part and a switching part arranged on the side far from the insertable part. The switching part includes a plurality of switching devices. The switching device arranged in the position nearest to the holding part among the plurality of switching devices includes a function of controlling sucking using the sucking tube path.

26 Claims, 25 Drawing Sheets (a) FREEZING (b) RELEASING

FIG.22

FIG. 28
FIG. 29
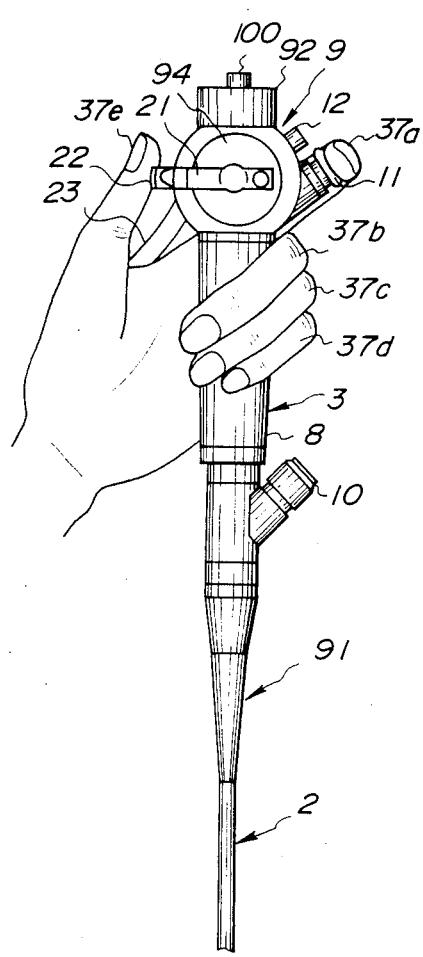
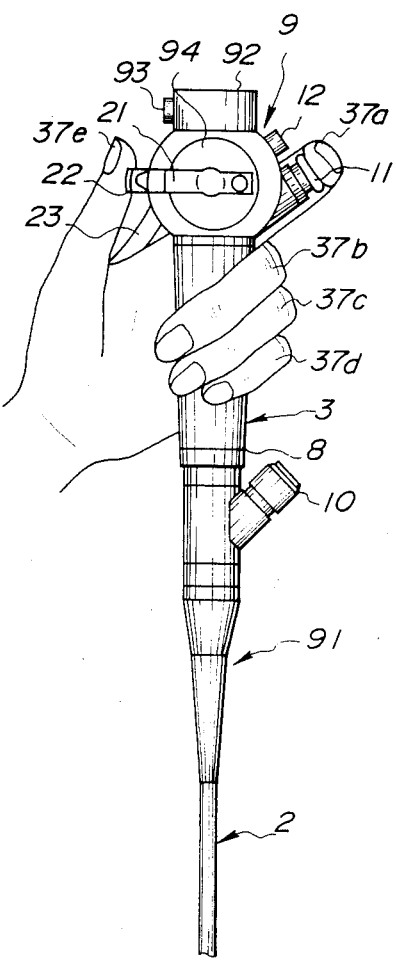

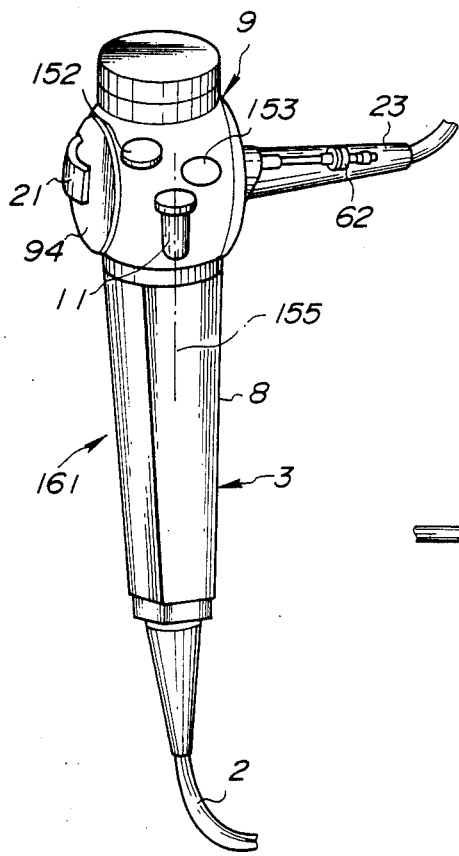
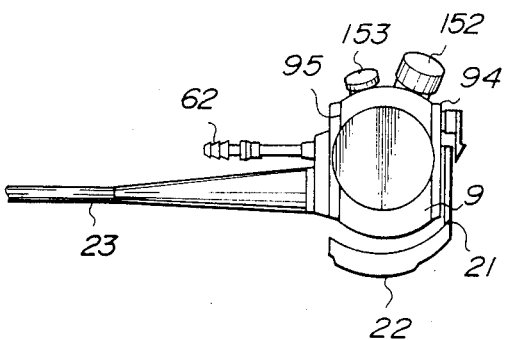

ENDOSCOPE

BACKGROUND OF THE INVENTION

1. Field of the Invention:

This invention relates to an endoscope having a plurality of switches in the operating part.

2. Related Art Statement:

Recently there is extensively used an endoscope (called also a scope or fiber scope) whereby organs within a body cavity can be diagnosed or inspected by inserting an elongate insertable part into the body cavity. There is used not only for industrial uses but also for medical uses an endoscope to observe or inspect an object within a boiler, machine, chemical plant pipe or device.

Further, there are also used various kinds of electronic scopes wherein such solid state imaging device as a charge coupled device (CCD) is used as an imaging means.

The above mentioned fiber scope or electronic scope is provided at the rear end of the insertable part with an operating part in which there are provided a holding part, sucking button, angle lever and various electrically controlled operating buttons. In the case of operating these buttons, the operator will hold the operating part by holding the holding part with the left hand and will operate the operating button with the left hand or right hand. However, the right hand will usually grip the insertable part and will make pushing, pulling and twisting operations and therefore the various operating buttons will be operated by the left hand holding the operating part. Further, the left hand thumb will normally operate the angle lever located on the back surface of the operating part, the middle finger, third finger and little finger will hold the holding part and therefore the various operating buttons will be operated by the left hand forefinger.

As shown in the publications of Japanese Patent Application Laid Open Nos. 182704/1983 and 197430/1988 and in U.S. Pat. No. 4,825,850, one or a plurality of operating buttons have been provided on the front surface of the operating part and have been arranged without taking their using frequency into consideration.

If the operating button can be operated only with the left hand forefinger as mentioned above, it will be necessary to arrange the operating button so as to be easily operated with the forefinger and to arrange the operating button highest in the using frequency in a position in which it can be most easily operated with the forefinger.

Also, in the above mentioned electronic endoscope, there is a case that an imaged image is recorded with a recording apparatus so as to be investigated in detail. The image is recorded in the recording apparatus generally with a still picture. Therefore, in the case of recording the image, releasing signals will be required to switch a moving picture to a still picture and to determine the timing of displaying and recording it. Such signals have been generated by switches provided in the operating part of the endoscope as described above.

However, as the kinds of the required signals increase with the forms of processing imaging signals becoming multiple, if switches are provided in response to the required signals as in the past, the number of switches provided in the operating part will also increase. Other operating buttons for sucking and the like must be provided. Thus, the operating part will become larger.

Particularly, in an endoscope for bronchial tubes, the number of operating buttons which can be provided in the operating part without reducing the operatability is limited to two. If more operating buttons than this are provided, the operatability will become very low.

For example, the left hand thumb operates the angle lever on the rear surface of the operating part and is used without being separated from the angle lever substantially during the inspection and the sucking and releasing must be made with the other fingers. Also, as the endoscope must be held, in fact, it must be able to be operated with one forefinger or with the forefinger and middle finger at most.

In the endoscope for bronchial tubes, the releasing and sucking are well used and further the freezing (stilling) is also used. Usually they are mostly used in the order of frequency of the sucking > releasing > freezing.

Therefore, there have been problems that, if as many buttons as the number of functions are provided, three operating buttons will be necessary, the operating part will become large and it will be very difficult to operate them without errors. That is to say, if there are three operating buttons, depending on such conditions as the position of the hand holding the operating part, the size of the hand and the length of the finger, unless the operating part is re-gripped, all the operating buttons will not be able to be operated in some case.

Particularly, if a plurality of operating buttons are arranged in the lengthwise direction of the operating part, the plurality of operating buttons will be operated with the forefinger by changing the angle with the middle finger with the third joint of the forefinger as a center. Therefore, if three or more operating buttons are arranged in the lengthwise direction of the operating part, it will be difficult to operate all the operating buttons without re-gripping the operating part.

OBJECTS AND SUMMARY OF THE INVENTION

An object of the present invention is to provide an endoscope high in the operatability of switches high in the using frequency.

Another object of the present invention is to provide an endoscope high in the operatability of a plurality of switches without making the operating part large.

An endoscope of the present invention comprises an elongate insertable part including an observing window at the tip and a sucking tube path through the interior, an image forming optical system receiving the light from an object to be imaged coming in through the above mentioned observing window and forming an endoscope image, an imaging means for imaging the above mentioned endoscope image formed by the above mentioned image forming optical system and an operating part provided as connected to the above mentioned insertable part in the base part on the side opposite the above mentioned tip. The above mentioned operating part includes a holding part arranged on the side near to the above mentioned insertable part and a switch part arranged on the side far from the above mentioned insertable part. The above mentioned switch part includes a plurality of switching means. The switching means arranged in the position nearest to the above mentioned holding part among the above mentioned plurality of switching means includes a function of controlling sucking using the above mentioned sucking tube path.

The other features and advantages of the present invention will become apparent enough with the following explanation.

BRIEF DESCRIPTION OF THE DRAWINGS

FIG. 1 is a side view of an endoscope.

FIG. 2 is a block diagram showing the formation of an endoscope apparatus.

FIG. 3 is a sectioned view of a first operating button and suction switching valve.

FIG. 4 is a sectioned view of a push botton in FIG. 3.

FIG. 5 is a sectioned view of a spring receiving member in FIG. 3.

FIG. 6 is a block diagram showing the formation of a video circuit in FIG. 2.

FIG. 7 is a sectioned view of a second operating button.

FIG. 8 is a circuit diagram showing an example of a part issuing freezing and releasing instructions within a controller.

FIG. 9 is a block diagram showing another example of the part issuing freezing and releasing instructions within the controller.

FIG. 10 is a timing chart for explaining the operation of the circuit in FIG. 9.

FIG. 11 is a block diagram of further another example of the part issuing freezing and releasing instructions within the controller.

FIG. 12 is an explanatory view showing an example of instructing signals memorized in an instructing signal discriminating reference table in FIG. 11.

FIG. 13 is an explanatory view showing an example of a switching signal discriminated by the circuit in FIG. 11.

FIG. 14 is a timing chart for explaining the operation of the circuit in FIG. 11.

FIG. 15 is a perspective view of an endoscope.

FIGS. 16 and 17 are respectively side views showing an operating part of an endoscope.

FIG. 18 is a block diagram showing the formation of a controlling apparatus.

FIG. 20 is a block diagram showing the formation of an endoscope apparatus.

FIG. 21 is a block diagram showing the formation of a video circuit.

FIG. 22 is a block diagram showing the formation of an endoscope apparatus in the fourth embodiment of the present invention.

FIG. 23 is a side view showing an operating part of an endoscope.

FIG. 24 is an explanatory view showing a head part of the endoscope in FIG. 23.

FIG. 25 is a block diagram showing the formation of an endoscope apparatus.

FIG. 26 is a block diagram showing the formation of a video circuit.

FIG. 27 is a perspective view of an endoscope.

FIG. 28 is a side view showing an operating part of an endoscope in the first modification of the fifth embodiment.

FIG. 29 is a side view showing an operating part of an endoscope in the second modification of the fifth embodiment.

FIGS. 31 to 35 relate to the sixth embodiment of the present invention.

FIG. 31 is a perspective view showing an operating part of an endoscope.

FIG. 32 is a side view showing an operating part of an endoscope.

FIG. 33 is a block daigram showing the formation of an endoscope apparatus.

FIG. 34 is a block diagram showing the formation of a video circuit.

FIG. 36 is a perspective view showing an operating part of an endoscope in the first modification of the sixth embodiment.

FIG. 37 is a plan view of an operating part of an endoscope in the second modification of the sixth embodiment.

DETAILED DESCRIPTION OF THE PREFERRED EMBODIMENTS

In FIGS. 1 to 14 is shown the first embodiment of the present invention.

In this embodiment, the present invention is applied to an endoscope for bronchial tubes.

Figure 2:
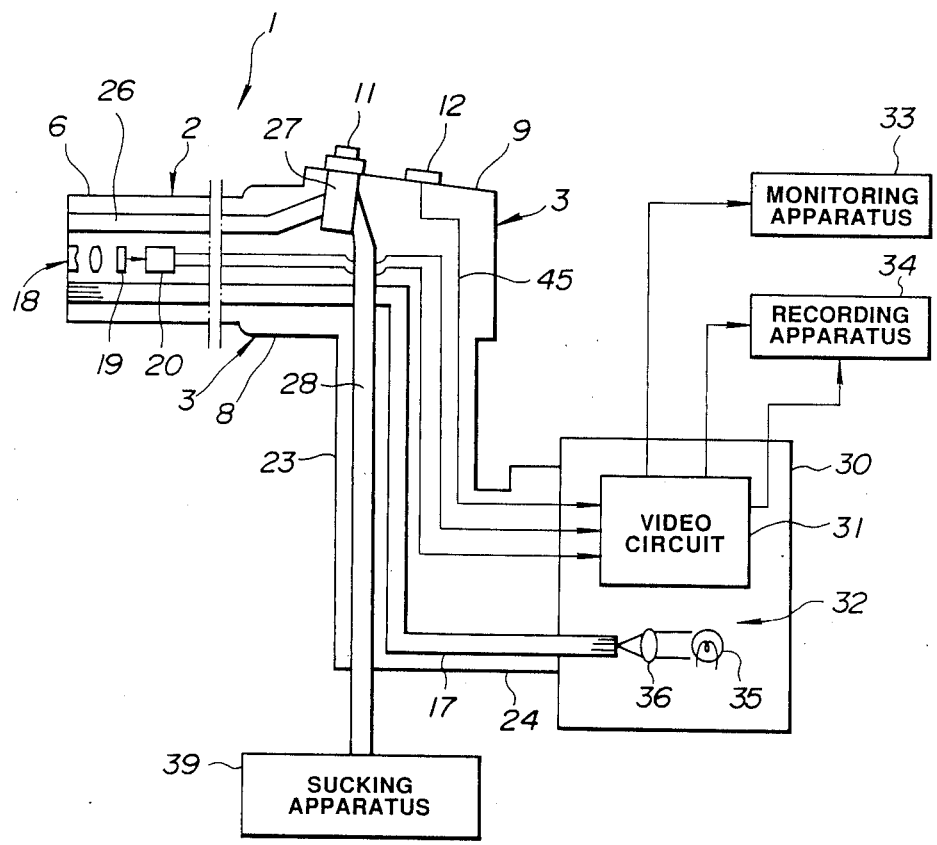

As shown in FIG. 2, the endoscope apparatus comprises an endoscope 1 for bronchial tubes, a controlling apparatus 30 to which this endoscope 1 is connected, a motor apparatus 33 and recording apparatus 34 connected to the above mentioned controlling apparatus 30 and a sucking apparatus 39 to which the above mentioned endoscope 1 is connected.

Figure 1:
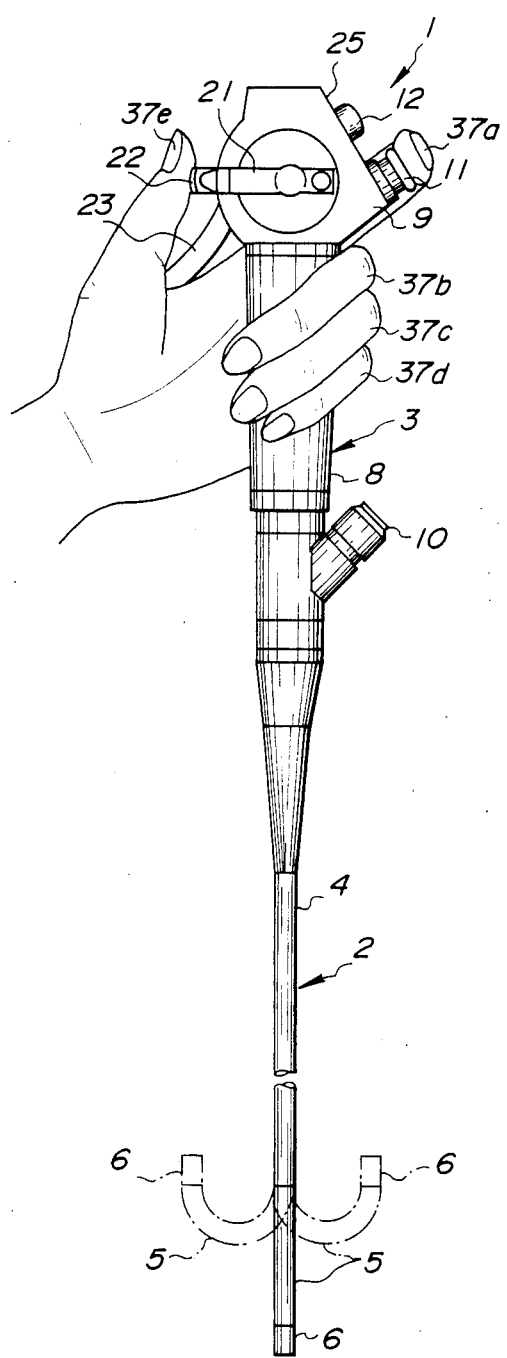
FIGS. 1 to 14 relate to the first embodiment of the present invention.

As shown in FIG. 1, the above mentioned endoscope 1 has an elongate flexible insertable part 2 to be inserted into a bronchial tube and an operating part 3 provided at one end (base part) of this insertable part 2. The above mentioned insertable part 2 is formed of a flexible part 4 on the base part side, a curvable part 5 provided as connected to this flexible part 4 at the tip and a rigid tip part 6 provided as connected to this curvable part 5 at the tip.

The above mentioned operating part 3 is provided with a holding part 8 arranged on the side near to the insertable part 2 and a switching part 9 arranged on the side farther from the insertable part 2 than the holding part 8. The above mentioned switching part 9 is provided on one side surface with an angle lever 21 for curving the above mentioned curvable part 5 and has a universal cord 23 as a connecting means for the operating part 3 and controlling apparatus 30 with each other extended out of the other side surface. Also, the insertable part 2 is provided within it with a channel (which may be also a sucking tube 26) through which a treating instrument or the like may be inserted and the above mentioned operating part 3 is provided in a position more on the side of the insertable part 2 than the holding part 8 with a treating instrument inserting port 10 communicating with the above mentioned channel.

The above mentioned angle lever 21 is formed to be like L, is rotatably supported at one end on one side surface of the above mentioned switching part 9 and is provided at the other end with a finger rest 22.

The wall surface 25 on the side opposite the above mentioned finger rest 17 of the above mentioned switching part 9 is such substantially flat slope as expands on the holding part 8 side and is provided on it with a first operating button 11 and second operating button 12 as a plurality of switching means substantially in the lengthwise direction (which is also the lengthwise direction of the operating part 3) of the insertable part 2. The above mentioned first operating button 11 is arranged on the side nearest to the holding part 8 among the plurality of operating buttons and the above mentioned second operating button 12 is arranged in a position farther from the holding part 8 than the above mentioned first operating button 11. Also, the above mentioned first operating button 11 is arranged immediately near to the end on the holding part 8 side in the switching part 9 and the above mentioned second operating button 12 is arranged in a position distinguishable in the operation from the first operating button 11 and near to the first operating button. The above mentioned first operating button 11 and second operating button 12 can be selectively operated with the forefinger of the hand holding the holding part 8, are both push buttons and are parallel in the pushing direction.

In this embodiment, the above mentioned operating button 11 is a suction controlling button highest in the using frequency in the endoscope for bronchial tubes among a plurality of functions operated by the plurality of operating buttons provided in the switching part 9. On the other hand, the above mentioned second operating button 12 is a push-button switch, for example, of two steps so that, when the first step is pushed, a freezing switch instructing an endoscope image to be a still picture will operate and, when the second step is pushed, a releasing switch instructing an endoscope image to be recorded as a still picture will operate and both functions of the freezing instruction and releasing instruction may be switched with each other.

Also, as shown in FIG. 2, on the tip surface of the above mentioned tip part 6, the sucking tube path 26 inserted through the insertable part 2 opens at one end and is connected at the other end to a suction switching valve 27 provided within the operating part 3. This suction switching valve 27 is integral with the above mentioned first operating button 11 controlling suction so that, by operating this first operating button 11, the suction switching valve 27 may be opened and closed. Further, the sucking tube path 28 is conneacated at one end with the suction switching valve 27, is inserted through the universal cord 23 and is connected to the sucking apparatus 39 through a connector 24 provided at the end of the universal cord 23.

Figure 3:
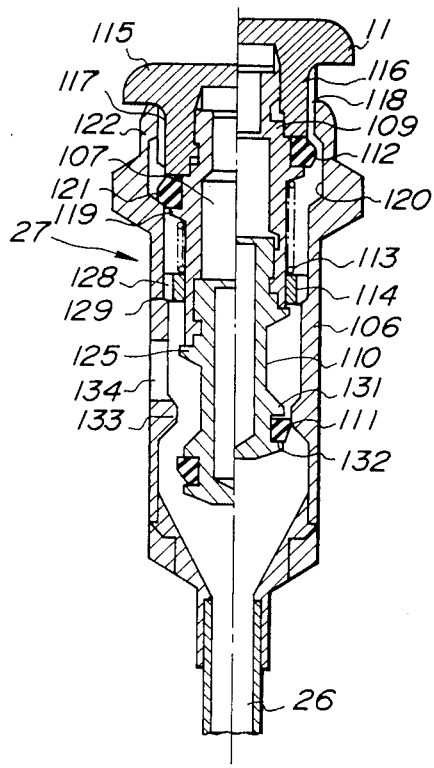

The above mentioned first operating button 11 and suction switching valve 27 are formed as shown, for example, in FIG. 3.

That is to say, the suction switching valve 27 has a cylinder 106 and piston 107, the cylinder 106 is fitted and bonded to the body of the switching part 9 and the piston 107 is removably fitted and inserted into the above mentioned cylinder 106. The above mentioned piston 107 has a first inner tube 109 and second inner tube 110. The second inner tube 110 is fitted with a first elastic member 111. The first inner tube 109 is fitted with a second elastic member 112, spring 113 and spring receiving member 114. A first operating button 11 is fitted to the upper part of the above mentioned first inner tube 109.

Figure 4:
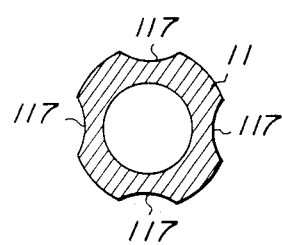

The first operating button 11 is fitted by screwing to the upper part of the first inner tube 109 and has a swollen part 115 in contact with the outer end of the cylinder 106 and a fitted part 116 fitting the inner periphery of the cylinder 106 and having a plurality of incisions 117 formed on the outer periphery as shown in FIG. 4 to form communicating gaps 118 with the inner peripheral surface of the cylinder 106.

The above mentioned second elastic member 112 is formed to be like a ring, is fitted to the upper outer periphery of the above mentioned first inner tube 109 and is held between the end surface of the first operating button 11 fitting part 116 and a flange 119 formed on the upper outer periphery of the first inner tube 109. As the cylinder 106 is formed to be peripherally recessed with a large diameter on the upper inner peripheral surface, the second elastic member 112 is not in sliding contact with the inner surface part 120 of the cylinder 106 and forms a gap with the inner surface part 120 but butts against a first step formed at the lower end of the inner surface part 120 of the cylinder 106 and a projection 122 on the opening inner surface formed at the upper end of the inner surface part 120.

Figure 5:
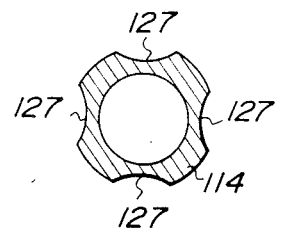

The first inner tube 109 and second inner tube 110 are screwed and connected with each other with the second inner tube 110 inside until the first inner tube 109 butts at the lower end against a flange 125 formed on the upper outer periphery of the second inner tube 110. An annular spring receiving member 114 is slidably fitted on the outer periphery of the first inner tube 109 at the lower end, is in sliding fit with the inner peripheral surface of the cylinder 106 and has a plurality of incisions 127 formed on the peripheral edge as shown in FIG. 5 so that communicating gaps 128 may be formed by these incisions 127 with the inner peripheral surface of the cylinder 106.

Further, a coil-like spring 113 is fitted to the outer periphery of the first inner tube 109, butts at the upper end against a flange 119 provided on the outer periphery of the first inner tube 109 at the upper end and butts at the lower end against a spring receiving member 114. That is to say, this spring 113 energizes the spring receiving member 114 downward. Therefore, as shown in FIG. 3, when the cylinder 106 and piston 107 are fitted, the spring receiving member 114 will always butt against a second step 129 formed on the inner periphery of the cylinder 106 so as to be engaged and positioned. However, in case the piston 107 is removed from the cylinder 106, the spring receiving member 114 will butt against the flange 125 provided on the second inner tube 110 and therefore will not be removed.

The ring-like first elastic member 111 is fitted as a flange on the outer periphery of the second inner tube 110 at the lower end, is held by two flanges 131 and 132 formed on the outer periphery of the second inner tube 110 at the lower end and is of the outside diameter larger than the inside diameter of the cylinder 106.

On the other hand, in the intermediate part of the above mentioned cylinder 106, as positioned below the above mentioned second step 129, a valve seat projection 133 within the cylinder is annularly formed in the peripheral direction. A sucking port 134 connected to the sucking tube path 28 leading to the sucking apparatus 39 is formed on the wall part positioned between this projection 133 within the cylinder and the above mentioned second step 125. The sucking tube path 26 is connected to the cylinder 106 at the inner end.

Within the cylinder 106, the second step 129 is smaller in the inside diameter than the first step 121 and further the projection 133 within the cylinder is smaller in the inside diameter than the second step 129. By the way, the projection 122 on the inside surface of the opening is of the same diameter as of the first step 121.

The operation of the above mentioned suction switching valve 27 shall be explained in the following.

First of all, when the sucking operation is not required, as shown on the right side of FIG. 3, the piston 107 will remain elevated by the energizing force of the spring 113. That is to say, the first elastic member 111 will contact the projection 133 as a valve seat within the cylinder to interrupt the communication of the sucking tube path with the inner space of the cylinder 106 above the projection 133 within the cylinder. Also, the sucking port 134 will communicate with the outside through the communicating gaps 118 and 128 respectively between the first operating button 11 and spring receiving member 114 and the inner peripheral surface of the cylinder 106 as formed by the respective incisions 117 and 127 of the first operating button 11 and spring receiving member 114. Therefore, the sucking force produced in the sucking port 134 will not act on the sucking tube path and will suck only the outside air.

When a suction is to be made, with the finger applied to the first operating button 11, the piston 107 is pushed in against the energizing force of the spring 113. Then, the second elastic member 112 will contact the first step 121 within the cylinder 106 so as to interrupt the inner space within the cylinder 106 from the outside. As the second inner tube 110 moves downward, the contact of the first elastic member 111 with the projection 133 within the cylinder will be released and the sucking tube path 26 and sucking port 134 will communicate with each other through the inner space. Therefore, the sucking force produced in the sucking port 134 will act on the sucking tube path 26 side and thereby the dirts within the body cavity will be able to be sucked and removed.

Figure 7:
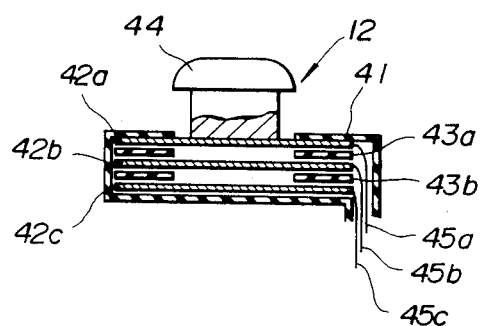

The above mentioned second operating button 12 is formed of a two-step switch as shown, for example, in FIG. 7. That is to say, three metal plates 42a, 42b and 42c are housed within an insulative cover 41. Insulative ring discs 43a and 43b are interposed respectively between the metal plates 42a and 42b and between the metal plates 42b and 42c. A pressing member 44 is fitted by bonding or the like to the central part of the uppermost metal plate 42a. Lead wires 45a, 45b and 45c are connected respectively to the metal plates 42a, 42b and 42c and are connected to the video circuit 31 within the controlling apparatus 30 through the universal cord 23 so that the conduction between the metal plates by pressing the second operating button 12 may be detected.

In this second operating button 12, if the operation, that is, the pressed amount of the first step is so small that the metal plate 42a may contact in the central part with the metal plate 42b, the lead wires 45a and 45b will be conductive with each other and this conductive state will be transmitted to the above mentioned video circuit 31. In this embodiment, freezing is instructed by the operation of this first step. When the second operating button 12 is pressed more strongly, the metal plate 42b pressed by the metal plate 42a will contact the lowermost metal plate 42c and the lead wires 45b and 45c will be conductive with each other. That is to say, in this case, the lead wires 45a, 45b and 45c will be conductive and this conductive state will be transmitted to the above mentioned video circuit 31. In this embodiment, releasing is instructed by the operation of this second step.

As shown in FIG. 2, the above mentioned universal cord 23 is provided at the end with a connector 24 removably connectable to the controlling apparatus 30 having a video circuit 31 and light source part 32. A monitoring apparatus 33 and a recording apparatus 34 consisting of a photographing apparatus or a disc cartridge type magnetic recording apparatus are connected to this controlling apparatus 30 so that an endoscope image may be thereby observed and recorded. The above mentioned photographing apparatus has a monitor within the body so that an endoscope image displayed in this monitor may be photographed with a camera. The above mentioned light source part 32 is provided with a light source lamp 35 so that the illuminating light output from this light source lamp 35 may be condensed by a condenser lens 36 and may be radiated on the entrance end surface of the light guide 17 provided in the connector 24. This light guide 17 is inserted through the universal cord 23 and insertable part 2 and is extended to the tip part 6 from which the illuminating light is radiated to an object to be imaged. The reflected light from the object is made to form an image on the imaging surface of a solid state imaging device 19 provided in the tip part 6 by an objective lens system 18 provided in the tip part 6 and the image is converted to an electric signal. A common mode rejection amplifier (abbreviated as a CMR amplifier hereinafter) 20 which is an amplifier high in the capacity of removing noises of the same phase component of an electric signal is connected to the above mentioned solid state imaging device 19. The output signal of the above mentioned solid state imaging device 19 is amplified by this CMR amplifier 20 and is delivered to the video circuit 31 within the controlling apparatus 30. By the way, one of the signal lines connecting the CMR amplifier 20 and video circuit 31 with each other is a dummy line for removing noises. In the above mentioned video circuit 31, the input electric signal is processed to be a video signal output to the monitoring apparatus 33 and recording apparatus 34.

The lead wire 45 (representing 45a, 45b and 45c) connected to the second operating button 12 provided adjacently to the above mentioned first operating button 11 is inserted through the universal cord 23 and is connected to the connector 24. The freezing signal and releasing signal generated by the above mentioned second operating button 12 are input into the video circuit 31 through the above mentioned lead wire 45. In this video circuit 31, when the freezing signal is input, the endoscope image of the moving picture displayed on the picture of the monitoring apparatus 33 will be made a still image and, when the releasing signal is input, the recording apparatus 23 will record a still image.

Figure 6:
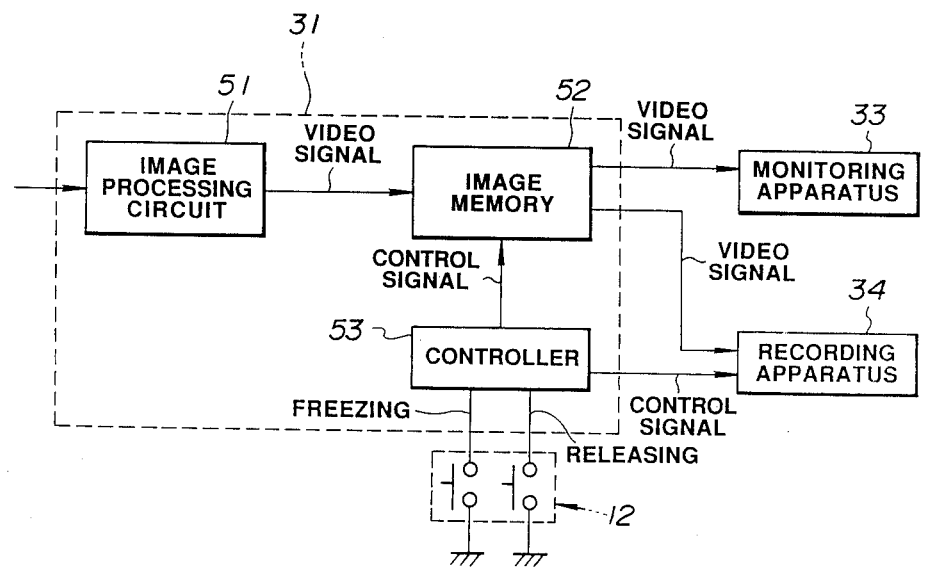

The above mentioned video circuit 31 is formed as shown, for example, in FIG. 6. That is to say, the video circuit 31 comprises an image processing circuit 51 whereby an image signal from the CMR amplifier is input and is made a video signal, an image memory 52 whereby the video signal from this image processing circuit 51 is memorized and a controller 53 whereby the freezing signal and releasing signal from the above mentioned second operating button are input and a control signal is transmitted to the above mentioned image memory 52 and recording apparatus 34. The above mentioned image memory 52 is controlled in writing and reading by the control signal from the above mentioned controller 53. The video signal read out of this image memory 52 is transmitted to the monitoring apparatus 33 and recording apparatus 34. By the above mentioned controller 53, when the freezing signal is input, the writing into the image memory 52 will be inhibited and the image will be frozen and, when the releasing signal is input, the recording apparatus 34 will be instructed to photograph or record the image.

The operation of this embodiment formed as in the above shall be explained in the following.

As shown in FIG. 1, the operator holds the holding part 8 with the middle finger 37b, third finger 37c and little finger 37d of the left hand, places the thumb 37e on the finger rest 22 and places the forefinger 37a on the first operating button 11. The right hand grips the insertable part 2 to push, pull and twist it.

The illuluminating light output from the light source lamp 35 of the light source part 32 is radiated onto the entrance end surface of the light guide 17 by the condenser lens 36 and is transmitted to the tip part 6. The illuminating light emitted from this tip part 6 is radiated onto an object to be imaged and the reflected light from this object is made to form an image on the imaging surface of the solid state imaging device 19 by the objective lens system 18. The optical image is converted to an electric signal by the solid state imaging device 19. The electric signal is output to the CMR amplifier, is amplified by this CMR amplifier 20 and is delivered to the video circuit 31. In this video circuit 31, a video signal is produced by the image processing circuit 51 and is output to the monitoring apparatus 33 and recording apparatus 34 through the image memory 52 and an endoscope image of a moving picture is displayed on the picture of the monitoring apparatus 33.

In the endoscope 1 for bronchial tubes, the first operating button 11 for controlling sucking is the highest in the using frequency but, in the case of operating this first operating button 11, as the forefinger 37a is always placed on the button 11, the button 11 will be able to be operated by only pushing it with this finger.

In the case of making the image a still image, the forefinger 37a is moved from the first operating button 11 to the second operating button 12 which is pushed in by one step. Then, this second operating button 12 will act as a freezing switch and a freezing signal will be transmitted from this second operating button 12 to the controller 53 within the video circuit 31. Then, this controller 53 will inhibit writing into the image memory 52 and will freeze the image. The video signal of the still image read out of this image memory 52 will be transmitted to the monitoring apparatus 33 and recording apparatus 34.

In the case of recording a still image, the second step of the second operating button 12 is pushed in. Then, this second operating button 12 will act as a releasing switch and a releasing signal will be transmitted from this second operating button 12 to the controller 53 within the video circuit 31. Then, this controller 53 will instruct the recording apparatus 34 to make recording. Thereby, the still image will be recorded by photographing or the like in the recording apparatus 34. By the way, in the case of recording an image with the above mentioned recording apparatus 34, the same as in freezing, the image may be made a still picture by the image memory 52.

Thus, in this embodiment, the first operating button 11 for controlling sucking highest in the using frequency among the plurality of operating buttons is provided in the position nearest to the holding part 8, that is, in the position most accessible by the forefinger 37a, is therefore easy to operate with the forefinger 37a and can be improved in the operatability. Also, as the second operating button 12 is provided near this first operating button 11, the buttons 11 and 12 can be selectively operated with the forefinger 37a without re-gripping the holding part 8 and are therefore high in the operatability.

Also, as the three functions of sucking, freezing and releasing can be made with the two operating buttons 11 and 12, the operating part 3 can be made small and light. Without re-gripping the holding part 8, the three functions can be controlled and the operatability is high.

As the pushing directions of the first operating button 11 and second operating button 12 are made parallel with each other, both buttons 11 and 12 are high in the operatability. Particularly, in case the distance between the first operating button 11 and second operating button 12 is very small, if the pushing directions of both buttons 11 and 12 are different from each other, when one of the first operating button 11 and second operating button 12 is pushed in, the other button will be likely to be also pushed by mistake.

Further, as the first operating button 11 and second operating button 12 are provided on the same surface 25 which is substantially a plane, in case the pushing directions of both operating buttons 11 and 12 are parallel with each other, the operator will be able to easily know the pushing directions of the respective operating buttons 11 and 12.

Here, three examples of the part issuing freezing and releasing instructions within the controller 53 shall be explained with reference to FIGS. 8 to 14.

Figure 8:
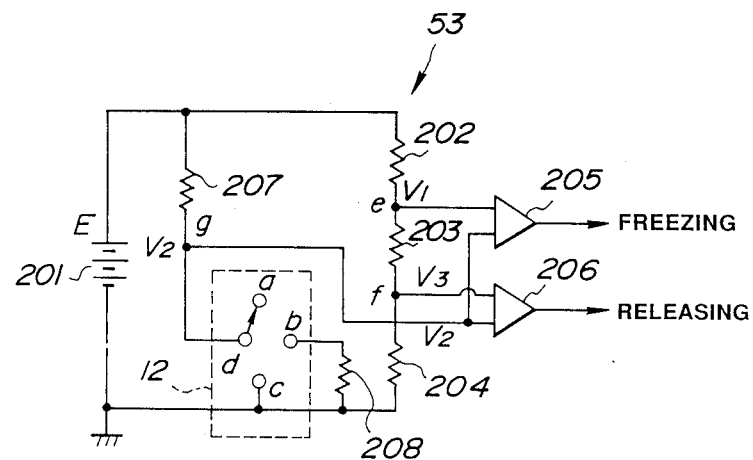

FIG. 8 shows the first example in which a direct current source 201 generating a voltage E is provided within the controller 53 and three resistances 202, 203 and 204 of the same resistance value are connectaed in series at both ends of this direct current source 201. The connecting point e of the resistances 202 and 203 is connected to one input end of a comparator 205 and the connecting point f of the resistances 203 and 204 is connected to one input end of a comparator 206. The other input end of the comparator 205 and the other input end of the comparator 206 are connected with each other and a resistance 207 is connected between these and the current source side end of the resistance 202. A series circuit of the second operating button 12 consisting of a two-step push-button switch and a resistance 208 (of the same resistance value as of the resistance 207) is connected between the output side end of the resistance 207 and the earthing line. The above mentioned second operating button 12 has three fixed contacts a, b and c and a movable contact d. A resistance 208 is connected between the contact b and earth and the contact c is directly earthed. The movable contact d is connected to the output signal end of the resistance 208. A freezing instructing signal to be transmitted to the image memory 52 is output from the comparator 205. A releasing instructing signal to be transmitted to the recording apparatus 34 is output from the comparator 206.

In such formation as in the above, when the second operating button 12 is not operated, the movable contact d will be connected to the fixed contact a, the voltage $V_2$ of the connecting point g of the resistance 207 and the movable contact d will be $V_2=E$, the voltage $V_1$ of the connecting point e will be $V_1=2E/3$ and the voltage $V_3$ of the connecting point f will be $V_3=E/3$. At this time, the converter 205 will be in the relation of $V_1<V_2$ and the comparator 206 will be in the relation of $V_2>V_3$. When $V_1>V_2$, the comparator 205 will generate an output signal. When $V_2<V_3$, the comparator 206 will generate an output signal. Therefore, in this stage, no freezing and releasing instructions will be output.

When the second operating button 12 is shallowly pushed to the first step, the movable contact d will contact the fixed contact b. As a result, the voltage of the connecting point g will become $V_2=E/2$ and will become lower than the voltage $V_1(=2E/3)$ of the connecting point e, the comparator 205 will act and a freezing instructing signal will be output from this comparator 205. At this time, as the comparator 206 will be in the relation of $V_2>V_3$, even if $V_2$ reduces, no releasing instructing signal will be generated.

Further, when the second operating button 12 is deeply pushed to the second step, the movable contact d will contact the fixed contact c. As a result, the voltage of the connecting point g will become $V_2=0$ and $V_2<V_3$ and therefore a releasing instructing signal will be output from the comparator 206. At this time, as the comparator 205 is kept in the relation of $V_1>V_2$, the freezing instructing signal will be kept on being output. Therefore, a still picture will be recorded in the recording apparatus 34.

When the finger is separated from the second operating button 12, the converters 205 and 206 will be returned sequentially to the initial state and the two instructions will vanish.

Figure 9:
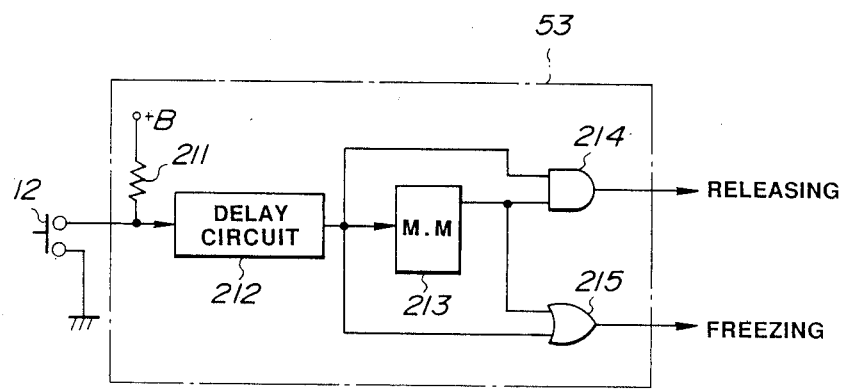
Figure 10:
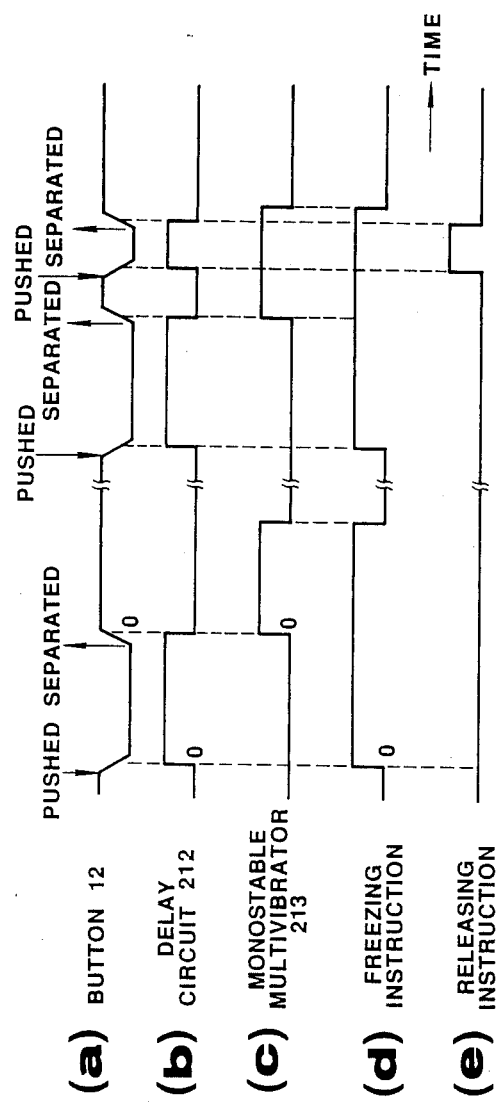

FIGS. 9 and 10 show the second example in which the second operating button 12 is a non-locked type push-button switch of one action. As shown in FIG. 9, a means for discriminating the operating pattern of the above mentioned second operating button 12 is provided within the controller 53. That is to say, the current source of voltage B is connected to one terminal of this second operating button 12 through a resistance 211 within the controller 53, a delay circuit 212 is connected and the other terminal is earthed. A monostable multivibrator (M.M) 213, one input end of an AND-gate 214 and one input end of an OR-gate are connected to the output terminal of the above mentioned delay circuit 212. The output end of the above mentioned monostable multivibrator 213 is connected to the other input end of the AND-gate 214 and the other input end of the OR-gate 215. The above mentioned monostable multivibrator 213 is to output an H level signal by the time determined by a preset time constant when the output signal of the delay circuit 212 falls.

The operation of the example shown in FIG. 9 shall be explained in the following with reference to FIG. 10.

As shown in FIG. 10(a), when the second operating button 12 is pushed, the resistance 211 will be earthed at the output side end, as shown in FIG. 10(b), the input end of the delay circuit 212 will be on a zero level and thereby a signal for an H level will be generated after a fixed time. As the output signal of this delay circuit 212 is applied to the OR-gate 215, a signal of an H level will be generated at the output end of this OR-gate 215 and will become a freezing instructing signal transmitted to the image memory 52 as shown in FIG. 10(d). This freezing instructing signal will be continuously generated while the second operating button 12 is pushed. When the finger is separated from the second operating button 12, as shown in FIG. 10(b), the output signal of the delay circuit 212 will be returned to the L level with some hysteresis but, as shown in FIG. 10(c), as synchronized with the fall of this waveform, an output signal of an H level will be generated from the monostable multivibrator 213. As the output signal of this monostable multivibrator 213 is applied to the OR-gate 215, even if the output signal of the delay circuit 102 is returned to the L level, a freezing instructing signal will be generated without being interrupted and will continue until the output of the monostable multivibrator 213 comes to the L level. On the other hand, as the output signal of the monostable multivibrator 213 is applied also to the AND-gate 214 but the output signal of the delay circuit 212 vanishes alternately, no logical condition will hold and, as shown in FIG. 10(e), no releasing instructing signal to be transmitted to the recording apparatus 34 will be output from the AND-gate 214.

However, in case the second operating button 12 is pushed again while the monostable multivibrator 213 is generating an H level output after the second operating button 12 is once separated, an H level voltage will be applied simultaneously to the two input ends of the AND-gate 214 and therefore a releasing instructing signal will be output from the AND-gate 214. At this time, as a signal of the same state as of the AND-gate 214 is applied also to the OR-gate 215 at the respective input ends, a logical condition will hold and a freezing instructing signal will be generated. Therefore, a still picture will be recorded in the recording apparatus 34.

Figure 11:
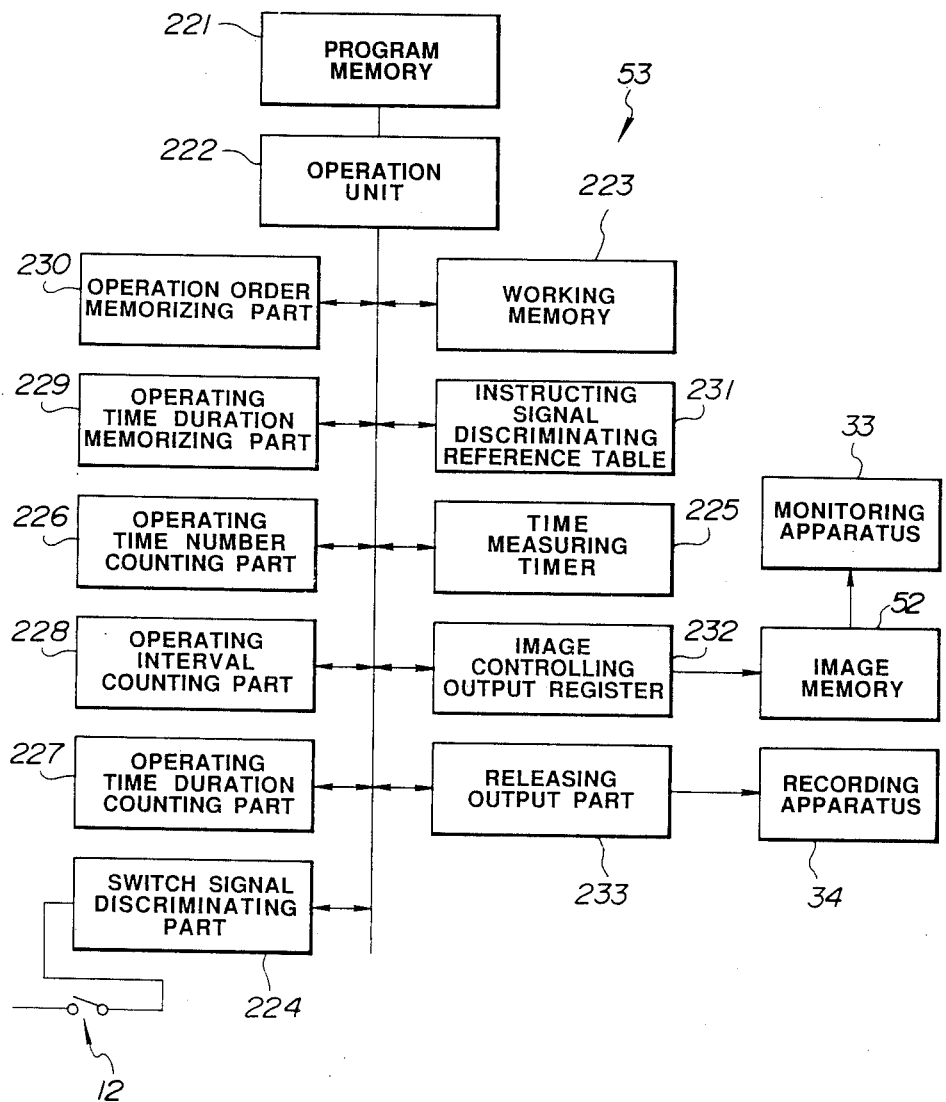
Figure 12:
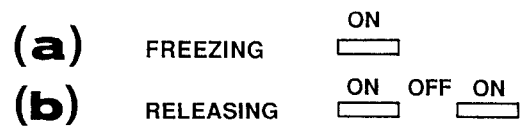

FIGS. 11 to 14 shown the third example in which the second operating button 12 is a non-locked type pushbotton switch of one action and such means for discriminating the operating pattern of the above mentioned second operating button 12 as is shown in FIG. 11 is provided within the controller 53. That is to say, as functionally seen, the controller 53 is formed as shown in FIG. 11. That is to say, the controller 53 is fundamentally provided with an operation unit 222 operated according to a system program of a program memory 221. A working memory 223, switching signal discriminating part 224, time measuring timer 225, operating time number counting part 226, operating time duration counting part 227, operating interval counting part 228, operating time duration memorizing part 229, operating order memorizing part 230, intructing signal discriminating reference table 231, image controlling output register 232 and releasing output port 233 are connected to a system bus connected to this operation unit 222.

The image memory 52 is connected to the image controlling output register 232 so as to receive a freezing instructing signal. The recording apparatus 34 is connected to the releasing output port 233 so as to receive a releasing instructing signal.

The second operating button 12 is connected to the switching signal discriminating part 224.

By the way, the above mentioned program memory 221, working memory 223, operating time number counting part 226, operating time duration counting part 227, operating interval counting part 228, operating time duration memorizing part 229, operation order memorizing part 230 and instructing signal discriminating reference table 231 are physically formed of memories within the controller. The operation unit 222, switching signal discriminationg part 224 and time measuring timer 225 are physically components within the controller.

In such controller 53, a table of such instructing signals as such freezing instructing signal and releasing instructing signal as are schematically shown in FIGS. 12(a) and 12(b) is digitally memorized in the instructing signal discriminating reference table 231. That is to say, the freezing instructing signal corresponds to once pushing the second operating button 12 as shown in FIG. 12(a) and the releasing instructing signal corresponds to continuously twice pushing the second operating button 12 as shown in FIG. 12(b).

Figure 13:
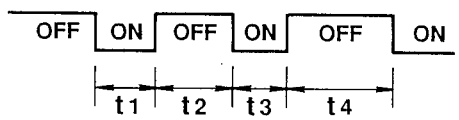

The discriminating algorism of the controller 53 when the switching signal generated by the on-off operation of the second operating button 12 is in the relation of the time width of $t_1$ to $t_4$ shown in FIG. 13 shall be explained in the following with reference to FIG. 14. By the way, in FIG. 13, $t_1$ represents the first on-time, $t_2$ represents the time from the first on to the second on, $t_3$ represents the second on-time and $t_4$ represents the time from the second on the third on.

Figure 14:
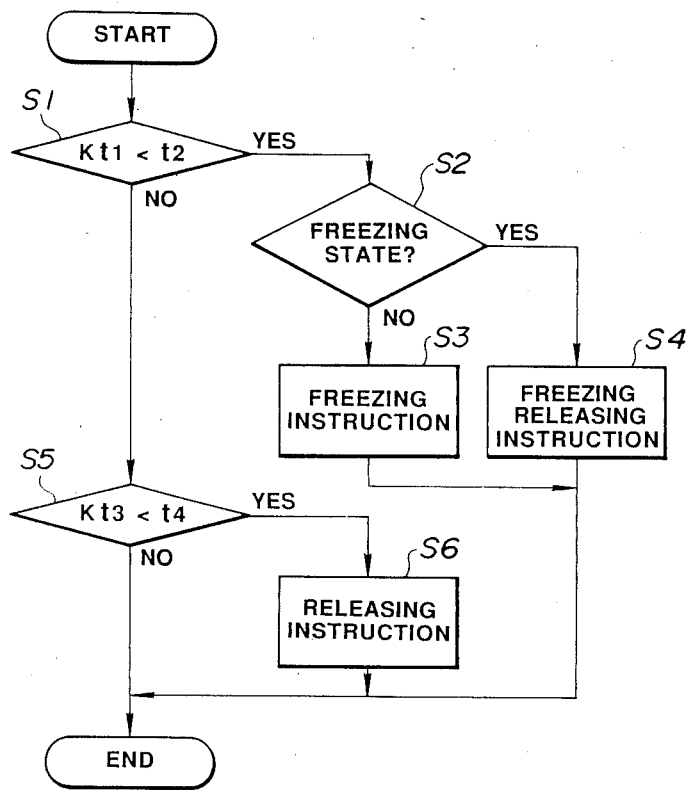

When the system program starts, the switching signal corresponding to the on-off operation of the second operating button 12 will be discriminated by the switching signal discriminating part 224, will be once memorized in the working memory 223 and then will be discriminated as shown in FIG. 14 by using the time measuring timer 225, operating time number counting part 226, operating time duration counting part 227, operating interval counting part 228, operating time duration memorizing part 229, operation order memorizing part 230 and instructing signal discriminating reference table.

That is to say, first of all, in the step S1, whether $kt_1 < t_2$ (k is, for example, about 1.5) is judged. In the case of YES, as shown in FIG. 12(a), it will be judged that the second operating button 12 will be once on and then will not be on for a time longer than the predetermined time ($kt_1$). In this case, in the step S2, whether in the freezing state or not will be judged. In the case of NO, in the step S3, a freezing instruction will be output from the image controlling output register 232 and the process will end. In the case of YES in the step S2, in the step S4, a freezing releasing instruction will be output from the image controlling output register 232 and the process will end.

On the other hand, in the case of NO in the step S1, in the step S5, whether $kt_3 < t_4$ or not will be judged. In the case of YES, as shown in FIG. 12(b), it will be judged that the second operating button 12 will be continuously twice on and then will not be on for a time longer than the predetermined time ($kt_3$). In this case, in the step S6, a releasing instructing signal will be output from the releasing output port 233 and the process will end. Also, in the case of NO in the step S5, the process will end.

Thus, when the second operating button 12 is once pushed, a freezing instructing signal will be output and, when the second operating button 12 is continuously twice pushed, a releasing instructing signal will be output.

In FIGS. 15 to 18 is shown the second embodiment of the present invention.

The endoscope 61 of this embodiment is different from the endoscope 1 of the first embodiment in respect of the shape of the switching part 9 and the number of the switches provided in this switching part 9.

Figure 15:
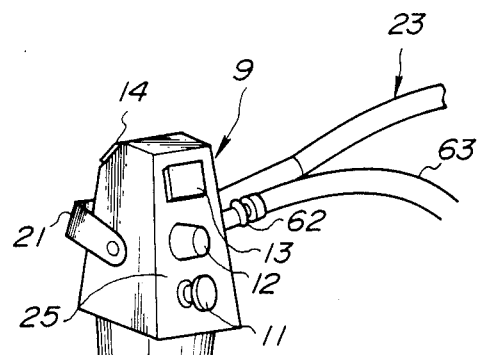
FIGS. 15 to 18 relate to the second embodiment of the present invention.
Figure 16:
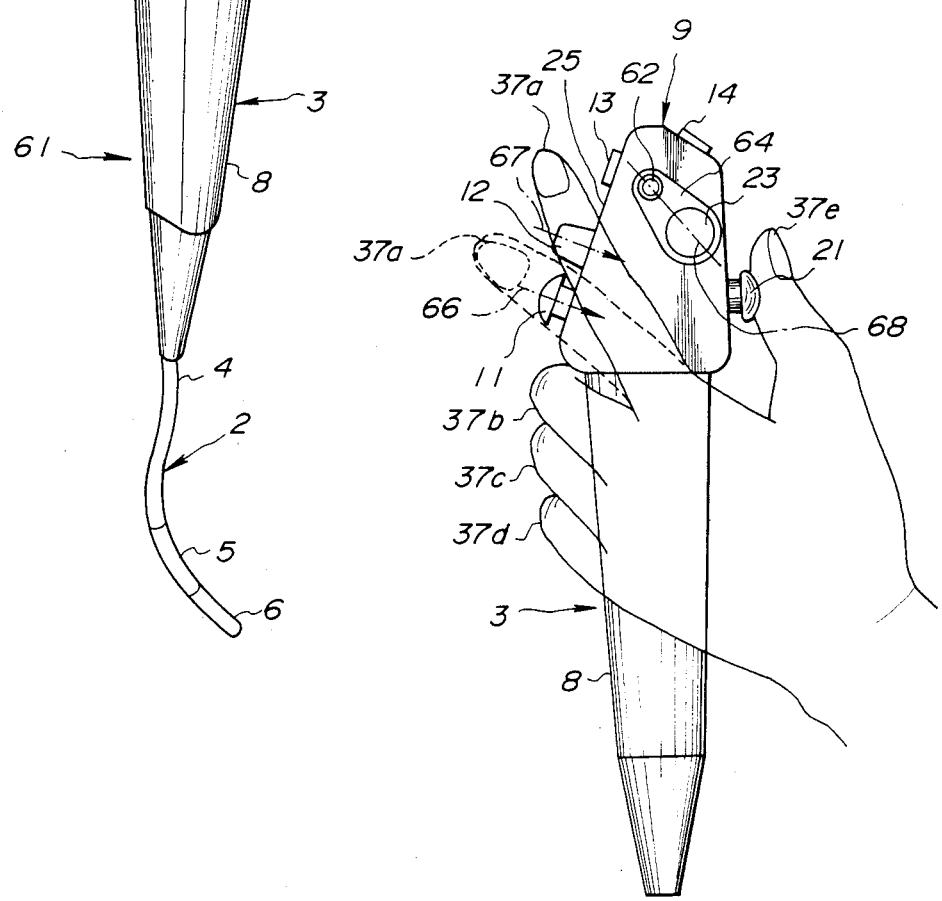

As shown in FIGS. 15 and 16, in the endoscope 61 of this embodiment, the wall surface 25 consisting of the plane slope of the switching part 9 of the operating part 3 is formed to be longer in the axial direction (lengthwise direction) of the insertable part 2 than in the first embodiment. On this wall surface 25, in the order from the holding part 8 side, the first operating button 11, second operating button 12 and third operating button 13 are provided in the axial direction (lengthwise direction) of the insertable part 2. Also, the fourth operating button 14 is provided on the upper part of the back wall on the side opposite the above mentioned wall surface 25.

Also, as shown in FIG. 16, a fitting base 64 is provided on the upper part of the left part of the left side surface in case the above mentioned wall surface 25 is made a front surface. On this fitting base 64, the universal cord 23 is fitted at the operating part 3 side end on the lower side (holding part 8 side) and a sucking mouthpiece 62 is fitted on the upper side (the side opposed to the holding part 8) of this universal cord 23, is connected to a suction switching valve 27 integral with the first operating button 11 and is to be connected to the sucking apparatus 39 through the sucking tube 63.

Figure 17:
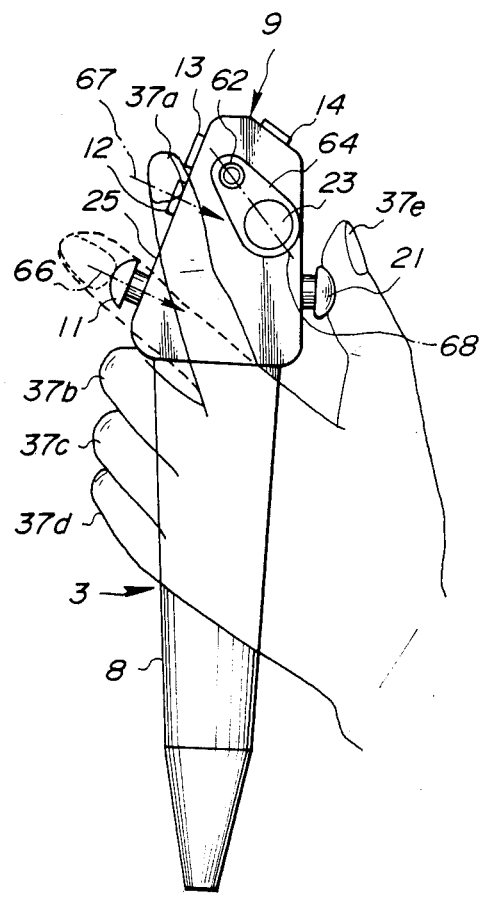

In this embodiment, the same as in the first embodiment, the first operating button 11 has a function of controlling sucking and the second operating button 12 has a function of instructing freezing and releasing. The above mentioned second operating button 12 may be a button operatable from all directions as shown in FIG. 16 or a push button determined in the pushing direction as shown in FIG. 17. By the way, for the button operatable from all directions can be used the one shown in the publication, for example, of Japanese Patent Application Laid Open No. 197430/1988. The third operating button 13 has a function of instructing to switch on/off a video tape recorder (abbreviated as VTR hereinafter). The fourth operating button 14 has a function of magnifying an endoscope image and switching a light amount. The above mentioned first, second and third operating buttons 11, 12 and 13 are provided on the same plane and the first operating button 11 pushing direction 66, the second operating button 12 pushing direction 67 and the third operating button 13 pushing direction are parallel with one another. By the way, in case the second operating button 12 is operatable from all directions, the pushing directions parallel with the pushing directions of the first and third operating buttons 11 and 13 will be included in the plurality of pushing directions of the second operation button 12.

As shown in FIGS. 16 and 17, the above mentioned first and second operating buttons 11 and 12 are arranged more on the insertable part 2 side than the imaginary plane including the respective center axes of the universal cord 23 and sucking mouthpiece 62. In other words, the indiversal cord 23 and sucking mouthpiece 62 are arranged by avoiding the forefinger 37 moving range so as not to be in the way when the first and second operating buttons 11 and 12 are pushed.

Figure 18:
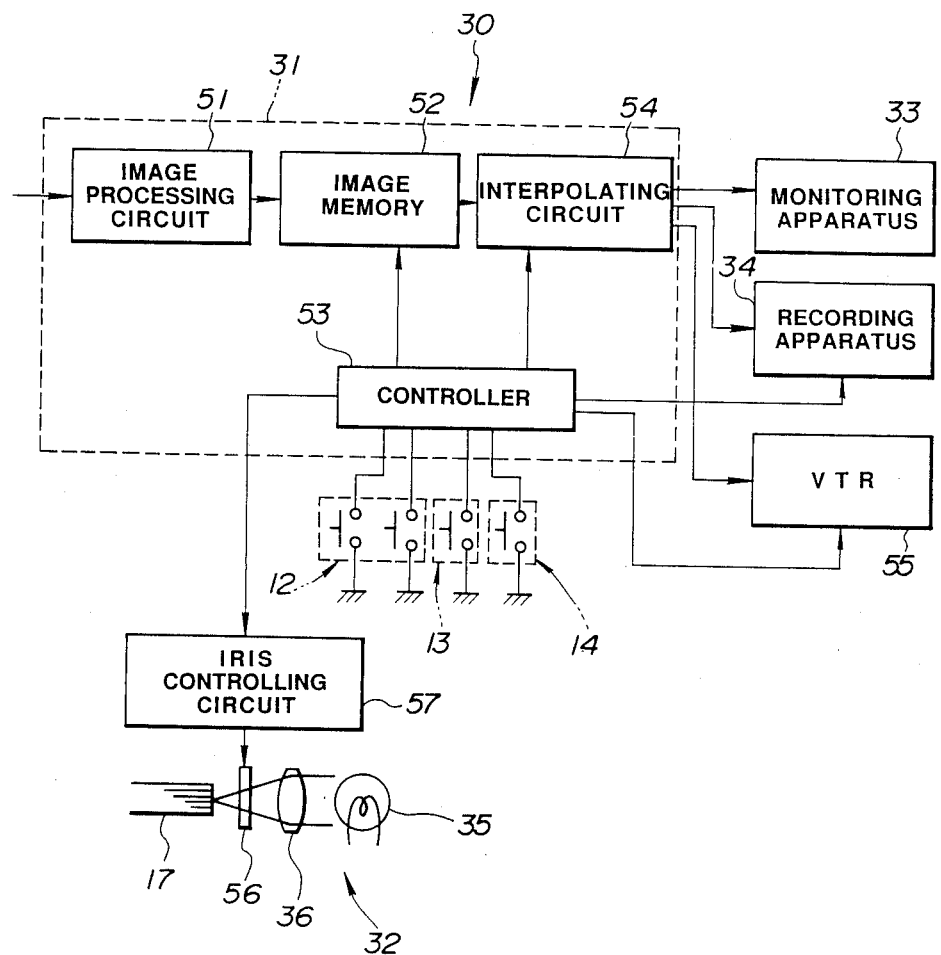

On the other hand, the controlling apparatus 30 is formed as shown in FIG. 18. That is to say, the video circuit 31 has an interpolating circuit 54 for interpolation when the image is magnified in the rear of the image memory 52 so that the output signal of this interpolating circuit 54 may be transmitted to the monitoring apparatus 33, recording apparatus 34 and VTR 55. The controller 53 is connected to the second, third and fourth operating buttons, 12, 13 and 14 and is to transmit a controlling signal to the image memory 52, interpolating circuit 54, recording apparatus 34, and VTR 55.

Within the light source apparatus 32, an iris 56 is provided between the condenser lens 36 and the entrance end of the light guide 17 and an iris controlling circuit 57 controlling this iris 56 is provided. The above mentioned controller 53 is to transmit a controlling signal also to the above mentioned iris controlling circuit 57.

The other formations are the same as in the first embodiment.

The operation of this embodiment shall be explained in the following

As shown in FIG. 16, the operator grips the holding part 8 with the three fingers of the middle finger 37b, third finger 37c and little finger 37d of the left hand, places the thumb 37e on the angle lever 21, places the forefinger 37a on the first operating button 11 highest in the using frequency and, as required, moves the forefinger 37a to the side opposite the holding part 8 to operate the second operating button. By the way, if the third operating button 13 can be operated by the forefinger 37a, it may be operated by the forefinger 37a or by the finger of the right hand.

In this embodiment, the same as in the first embodiment, freezing and releasing are instructed by the operation of the second operating button 12. Further, when the third operating button 13 is operated, a control signal instructing on/off will be transmitted from the controller 53 to the VTR 55. In case the fourth operating button 14 has a function of instructing to magnify the endoscope image, when this fourth operating button 14 is operated, the controller 53 will control the reading out of the image memory 52 and the operation of the interpolating circuit 54 to magnify the endoscope image. In case the fourth operating button 14 has a function of instructing to switch the light amount, when this fourth operating button 14 is operated, the controller 53 will control the iris controlling circuit 57 to switch the illuminating light amount.

The other operations and effects are the same as in the first embodiment.

Figure 19:
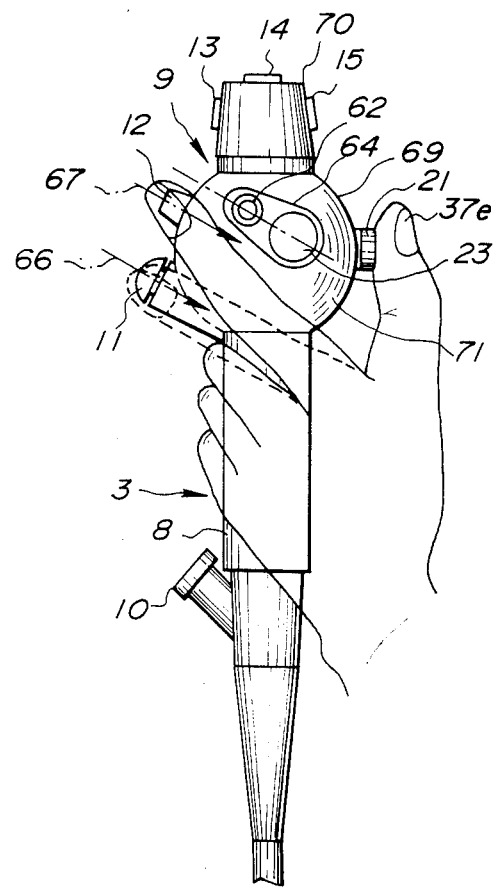
FIG. 19 is a side view showing an operating part of an endoscope in a modification of the second embodiment.

In FIG. 19 is shown a modification of the second embodiment.

The endoscope of this modification is different from the endoscopoe of the second embodiment in respect of the shape of the switching part 9 and the number of switches provided in this switching part 9.

In the endoscope of this modification, the switching part 9 has a spherical first switching part 69 and a second switching part 70 provided on the side opposite the holding part 8 of this first switching part 69. On one side surface of the above mentioned first switching part 69, in the order from the holding part 8 side, the first operating button 11 and second operating button 12 are provided in the axial direction of the insertable part 2. A finger resting part of the angle lever 21 is arranged on the side of the first switching part 69 on the side opposite the above mentioned first and second operating buttons 11 and 12. On the upper part of the left side surface in the case that the first and second operating buttons 11 and 12 side is made a front surface, a fitting base 64 is provided and the universal cord 23 and sucking mouthpiece 62 are provided on this fitting base 64. The position relations of the above mentioned first and second operating buttons 11 and 12, angle lever 21, universal cord 23 and sucking mouthpiece 62 and the pushing directions of the first and second operating buttons 11 and 12 are the same as in the second embodiment.

In the above mentioned second switching part 70, a third operating button 13 is provided on the first and second operating buttons 11 and 12 side, a fourth operating button 14 is provided at the top and a fifth operating button 15 is provided on the opposite side of the third operating button 13.

In this modification, the first operating button 11 has a function of controlling at least sucking and the second operating button 12 has a function of instructing freezing. The third operating button 13 has a function of instructing a light measuring system to be switched and a printer to be on/off, the fourth operating button 14 has a function of instructing the VTR to be on/off and the fifth operating button 15 has a function of instructing releasing.

The other formations, operations and effects are the same as in the second embodiment.

Figure 20:
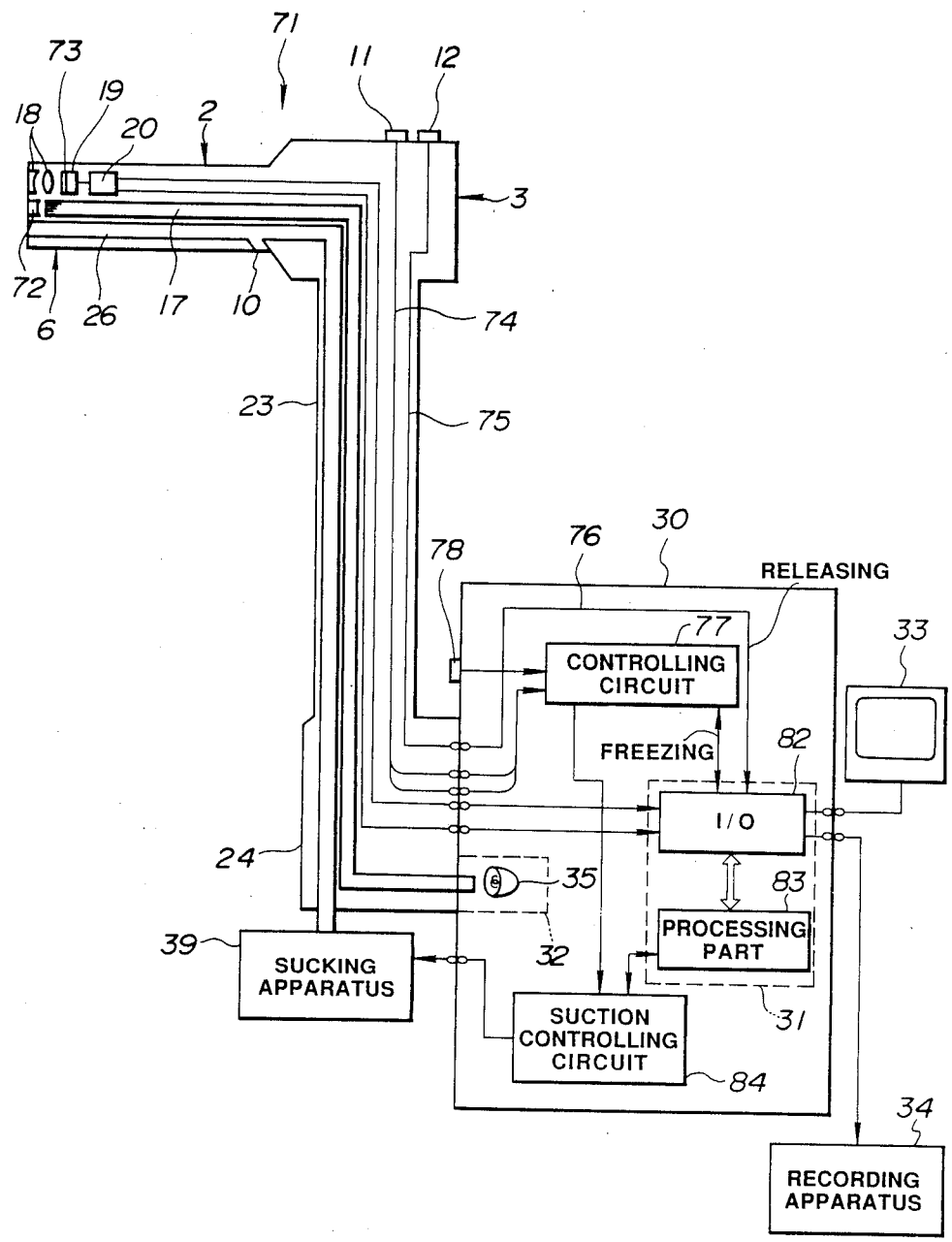
FIGS. 20 and 21 relate to the third embodiment of the present invention.
Figure 21:
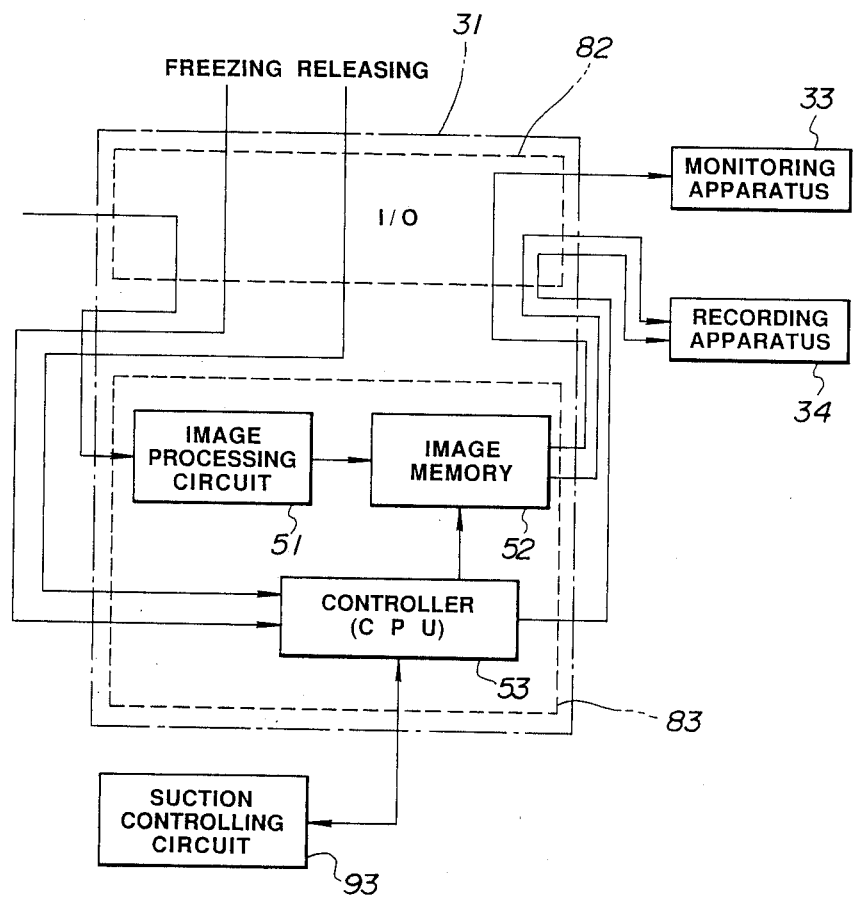

In FIGS. 20 and 21 is shown the third embodiment of the present invention.

The appearance of the endoscope 71 in this embodiment is the same as in FIG. 1.

As shown in FIG. 20, in this embodiment, the sucking tube path 26 inserted through the insertable part 2 is also a treating instrumental channel, is extended to the connector 24 without having a suction switching valve 27 interposed in the course and is connected to the outside sucking apparatus 39 through this connector 24. In the tip part 6 of the insertable part 2, an illuminating lens 72 is provided as opposed to the exit end surface of the light guide 17. A color separating mosaic filter 73 is fitted to the front surface of the solid state imaging device 19.

In this embodiment, the first operating button 11 is a push-button switch of two steps and performs two functions of instructing freezeing and controlling sucking. Also, the second operating button 12 instructs releasing.

On the other hand, a controlling apparatus 30 is provided with a video circuit 31, light source part 32, controlling circuit 77, suction controlling circuit 84 and a mode switching switch 78 connected to the above mentioned controlling circuit 77.

The first operating button 11 of the above mentioned endoscope 71 is to be connected to the above mentioned controlling circuit 77 through a signal line 74. This controlling circuit 77 is connected to the above mentioned video circuit 31 and suction controlling circuit 84. In response to the operation of the first operating button 11, the above mentioned controlling circuit 77 outputs a freezing signal to the video circuit 31 or a sucking operation instruction controlling signal to the suction controlling circuit 84 which is connected to the above mentioned sucking apparatus 39 to control it.

The above mentioned second operation button 12 is connected to the above mentioned video circuit 31 through a signal line 75 to transmit a releasing signal to this video circuit 31.

The above mentioned first operating button 11 and controlling circuit 77 can be formed the same as in the second operating button 12 and controller 53 shown in FIGS. 7, 8 to 10 and 11 to 14 in the first embodiment. That is to say, in response to the first operating button 11 pressing state and operating pattern, a freezing signal or sucking operation instruction controlling signal is output from the controlling circuit 77.

In response to the switching of the mode switching switch 8, the above mentioned controlling circuit 77 is selectively set in one of the later described two modes.

The video circuit 31 in this embodiment is formed as shown in FIG. 21.

That is to say, the video circuit 31 is provided with an input/output circuit (which shall be mentioned as an I/O circuit hereinafter) 82 and a processing part 83. The above mentioned processing part 83 comprises an image processing circuit 51 in which an image signal from the CMR amplifier 20 is input through the I/O circuit 82 and is made a video signal, an image memory 52 memorizing the video signal from this image processing circuit 51 and a controller 53 inputting a freezing signal from the controlling circuit 77 and a releasing signal from the second operating button 12 through the I/O circuit 82 and transmitting a control signal to the above mentioned image memory 52 and recording apparatus 34. By the way, the control signal from the controller 53 is transmitted to the recording apparatus 34 through the I/O circuit 82. The above mentioned image memory 52 is controlled in writing and reading by the control signal from the above mentioned controller 53. The video signal read out of this image memory 52 is transmitted to the monitoring apparatus 33 and recording apparatus 34 through the I/O circuit 82. The above mentioned controller 53 consists, for example, of a CPU so that, when a freezing signal is input, writing into the image memory 52 will be inhibited and the image will be frozen and, when a releasing signal is input, the recording apparatus 34 will be instructed to record an image as by photographing. The above mentioned controller 53 controls also the suction controlling circuit 93.

The other formations are the same as in the first embodiment.

The operation of this embodiment shall be explained in the following.

First of all, the case that one mode (which shall be mentioned as a mode A hereinafter) is set by the mode switching switch 78 shall be explained. In case the first operating button 11 is such push-button switch of two steps as is shown in FIG. 7, when this first operating button 11 is pushed in by one step, this operation will be judged by the controlling circuit 77 which will output a freezing signal to the video circuit 31. That is to say, in the mode A, the operation of the first step of the first operating button 11 will act as a freezing switch. On the other hand, in case the first button 11 is pushed at once into the second step (for example, the movement from the first step to the second step takes less than 0.2 second), this operation will be judged by the controlling circuit 77 to be the second step operation. In this case, the controlling circuit 77 will output to the suction controlling circuit 84 a control signal instructing sucking. That is to say, in the mode A, the operation of the second step of the first operating button 11 will act as a suction controlling switch. With the above mentioned controlling signal, the suction controlling circuit 84 will set the sucking apparatus 39 in the operating state so that sucking may be made by the sucking apparatus 39 through the sucking tube path 26.

In this sucking state, when the finger is separated from the first operating button 11, sucking will be stopped (released).

By the way, by the operation in the first step of this first operating button, freezing is instructed to display a still picture. When the operation in the first step is made once again, the freezing state will be released. When the button is pushed to the first step, after more than a predetermined time elapses from the operation in the first step, even if the operation in the second step is made, no sucking will be made.

Thus, in the mode A, the operation in the first step of the first operating button 11 will perform the function of instructing freezing to be on/off and the operation in the second step will perform the function of instructing sucking.

The case of setting the other mode (mentioned as the mode B hereinafter) with the mode switching switch 78 shall be explained in the following. In case the first operating button 11 is such push-button switch of two steps as is shown in FIG. 7, when this first operating button 11 is pushed by one step, the same as in the case of the mode A, this operation will be judged in the controlling circuit 77 which will output a freezing signal to the video circuit 31. On the other hand, when the first operating button 11 is further strongly pushed in so that the operating state in the first step may become the operating state in the second step, the controlling circuit 77 will release freezing with the rise of the operation in the second step and then will output a controlling signal for sucking so that the sucking apparatus 39 may suck through the sucking tube path 26. If the finger is separated from the first operating button 11 in this state, sucking wll stop.

Thus, in this embodiment, as sucking and freezing can be simultaneously made, sucking can be prevented from being blindly made in the freezing state and the safety can be secured.

The other operations and effects are the same as in the first embodiment.

By the way, the above explained third embodiment may be applied to the endoscopes in the second embodiment shown in FIGS. 15 to 18 and the modification of the second embodiment shown in FIG. 19. That is to say, the first operating button 11 of the endoscope shown in these drawings may be made a push-button switch of two steps wherein the operation in the first step is to function to instruct freezing and the operation in the second step is to function to control sucking and the second operating button 12 may have a function of instructing releasing.

Figure 22:
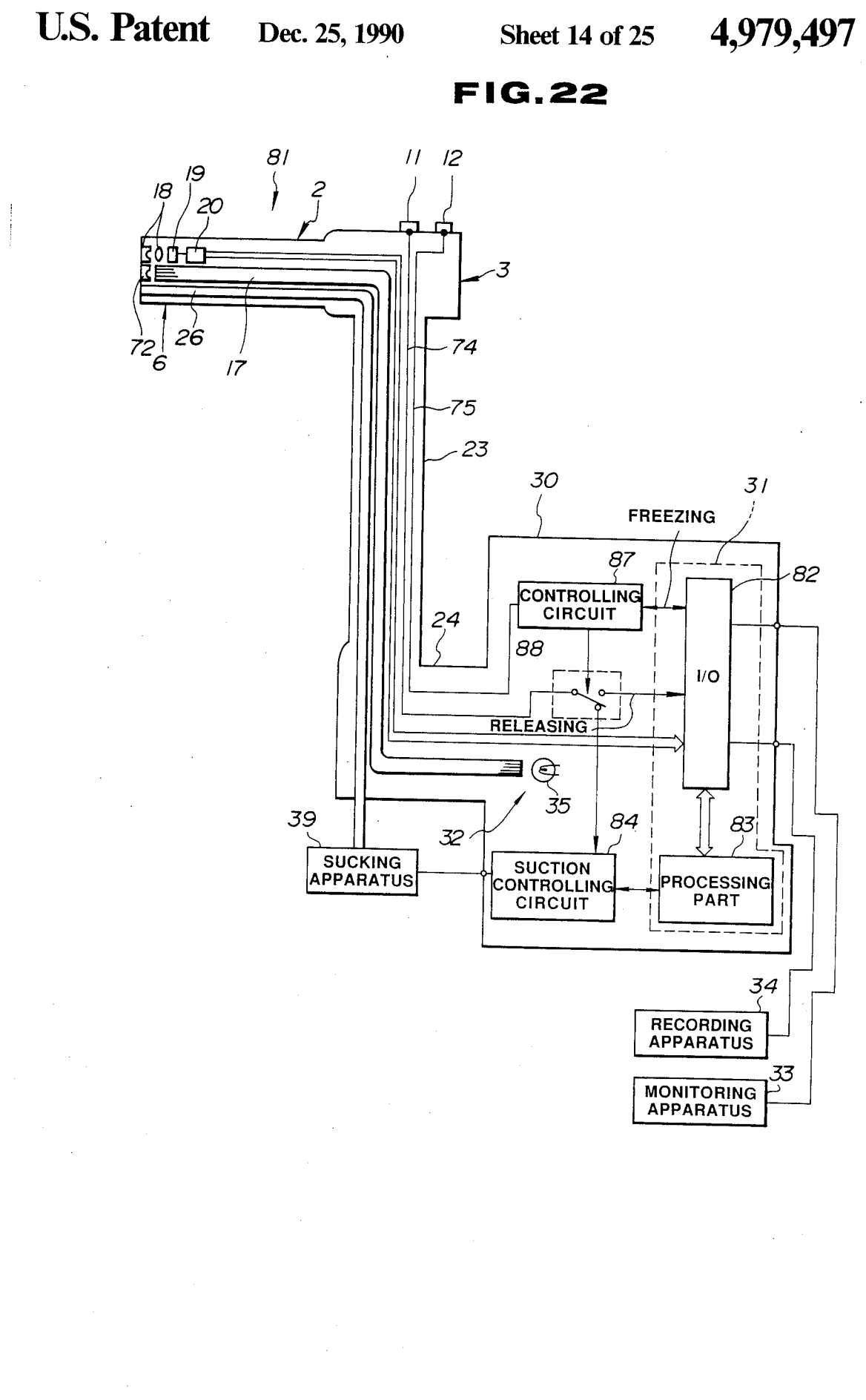

In FIG. 22 is shown the fourth embodiment of the present invention.

The appearance of the endoscope 81 in this embodiment is the same as of the endoscope 1 shown in FIG. 1.

As shown in FIG. 22, in this embodiment, the sucking tube path 26 inserted through the insertable part 2 is extended to the connector 24 without the suction switching valve 27 interposed in the cource and is connected to the outside sucking apparatus 39 through the connector 24.

The controlling apparatus 30 is provided with a video circuit 31, light source part 32, controlling circuit 87, suction controlling circuit 84 and selector 88 of one input and two outputs.

The first operating button 11 of the above mentioned endoscope 81 is connected to the above mentioned selector 88 at the input end through a signal line 74. This selector 88 is connected at one output end to the video circuit 30 and at the other output end to the suction controlling circuit 84. The above mentioned suction controlling circuit 84 is connected to the above mentioned sucking apparatus 39 to control it. The second operating button 12 is connected through a signal line 75 to the above mentioned controlling circuit 87 which outputs a freezing signal to the video circuit 30 in response to the operation of the above mentioned second operating button 12 and transmits a switching signal to the above mentioned selector 88. That is to say, when the second operating button 12 is not pushed, the controlling circuit 87 will not output a switching signal to the selector 88 in which the input end will be connected with the suction controlling circuit 84 side output end. In this state, the signal by the pressing operation of the first operating button 11 will be input into the suction controlling circuit 84 as a suction controlling signal. On the other hand, when the second operating button 12 is pushed, the controlling circuit 87 will output a switching signal to the selector 88 in which the input end will be connected with the video circuit 31 side output end. In this state, the signal by the pressing operation of the first operating button 11 will be input into the video circuit 31 as a relay signal.

The video circuit 31 in this embodiment is formed the same as is shown in FIG. 21 of the second embodiment.

The other formations are the same as in the first embodiment.

The operation of this embodiment shall be explained in the following.

When the second operating button 12 having a function of instructing freezing is pushed, the controlling circuit 87 will sense it and will output a freezing signal to the video circuit 31 so that the image displayed in the monitoring apparatus 33 may be made a still picture.

In this embodiment, the function of the first operating button 11 will be switched in response to the state of this second operating button 12. When the above mentioned second operating button 12 is not pushed, by the control of the controlling circuit 87, the input end of the selector 88 will be connected to the suction controlling circuit 84 side output end. In this state, the signal by the pressing operation of the first operating button 11 will be input into the suction controlling circuit 84 as a suction controlling signal so that sucking may be made by the sucking apparatus 39 through the sucking tube path 26. On the other hand, when the second operating button 12 is pushed, the input end of the selector 88 will be connected with the video circuit 30 side output end. In this state, the signal by the pressing operation of the first operating button 11 will be input into the video circuit 30 as a releasing signal so that a still picture may be recorded in the recording apparatus 34.

By the way, the second operating button 12 may be a switch of a type in which the pressed state is locked or a non-locked type switch so that, in the controlling circuit 87, until the second operating button 12 is pushed next, the second operating button 12 will remain pressed and, when it is pushed next, it will be released.

Thus, in this embodiment, the first operating button 11 will have a suction controlling function when the second operating button 12 is not pushed, that is, in the freezing released state but will have a releasing instructing function when the second operating button 12 is pushed, that is, in the frozen state.

Therefore, according to this embodiment, as the suction controlling function will not act when frozen, it can be prevented to suck blindly in the frozen state and the safety can be secured.

The other operations and effects are the same as in the first embodiment.

By the way, the above explained fourth embodiment may be applied to the endoscopes in the second embodiment shown in FIGS. 15 to 18 and the modification of the second embodiment shown in FIG. 19. That is to say, the second operating button 12 of the endoscope shown in these drawings may have a freezing instructing function and the first operating button 11 may have a releasing function only when the second operating button 12 is operated and may have a suction controlling function in other states.

In FIGS. 23 to 27 is shown the fifth embodiment of the present invention.

Figure 23:
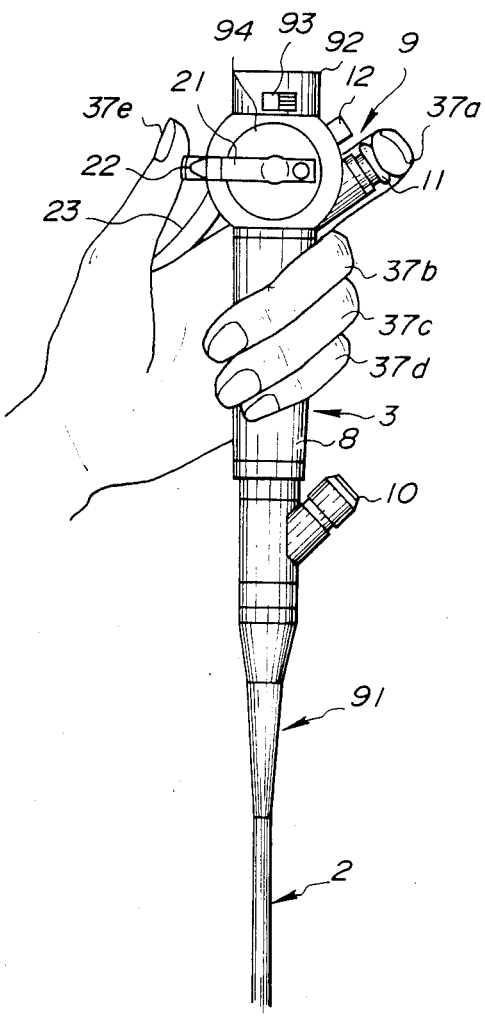
FIGS. 23 to 27 relate to the fifth embodiment of the present invention.
Figure 27:
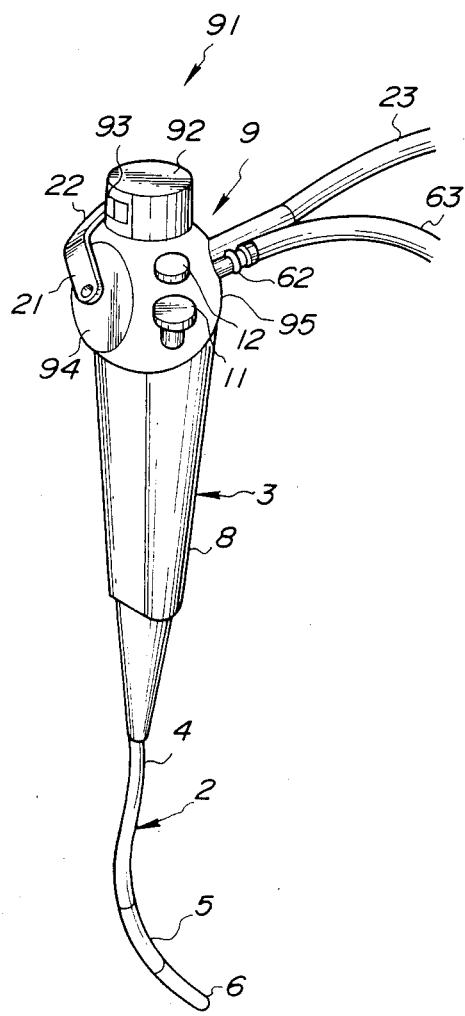

As shown in FIGS. 23 and 27, the appearance of the endoscope 91 in this embodiment is similar to that of the embodiment 1 in the first embodiment but the shape of the switching part 9 is different. That is to say, the switching part 9 is formed to be substantially spherical, is incised in the side parts of the sphere and has planes 94 and 95 formed to be opposed to each other and substantially parallel with the lengthwise direction of the insertable part 2. On one plane 94, an angle lever 21 is provided and, from the other plane 95, such universal cord 23 and sucking mouthpiece 62 as are shown in FIG. 27 are extended out.

The position relations of the first operating button 11, second operating button 12 and angle lever 21 provided in the above mentioned switching part 9 are the same as in the first embodiment.

In this embodiment, the same as in the first embodiment, the first operating button 11 has a suction controlling function. On the other hand, the second operating button 12 has two functions of instructing freezing and releasing.

Figure 24:
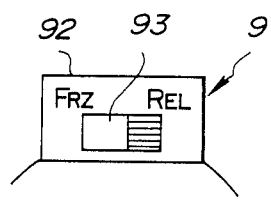

Also, in this embodiment, the above mentioned switching part 9 is provided at the end opposite the insertable part side with a substantially columnar head 92. As shown in FIG. 24, a releasing and freezing switching switch 93 as a means for switching the function of the above mentioned second operating button 12 is provided in a position on the plane 94 side on which the above mentioned angle lever 21 is rotatably indicated on the peripheral wall of this head 92.

Figure 25:
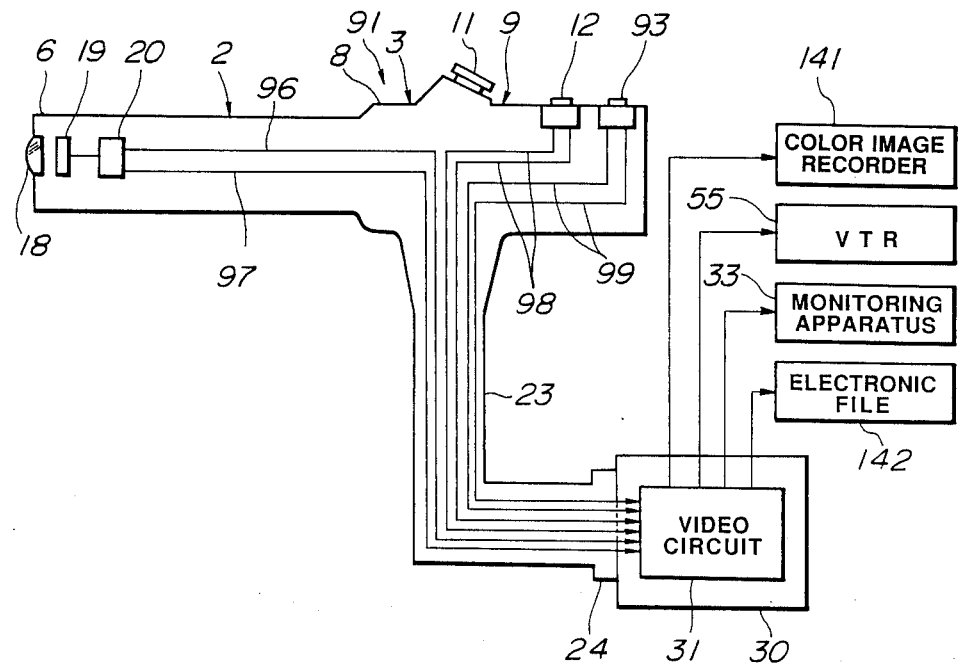

As shown in FIG. 25, the endoscope 91 is connected to a controlling apparatus 30 having a video circuit 31 by a connector 24 provided at the end of the universal cord 23. The above mentioned second operating button 12 is connected to the above mentioned video circuit 31 through signal lines 98. The above mentioned releasing and freezing switching switch 93 is connected to the above mentioned video circuit 31 through signal lines 99. By the way, though not illustrated in FIG. 25, the light source part 32 within the controlling apparatus 30, the light guide 17, sucking tube paths 26 and 28 and suction switching valve 27 within the endoscope 91 and the sucking apparatus 39 connected to the above mentioned sucking tube path 28 are the same as in the first embodiment.

A color image recorder 141 as a recording apparatus, VTR 55, electronic file 142 and monitoring apparatus 33 are connected to the above mentioned controlling apparatus 30.

Figure 26:
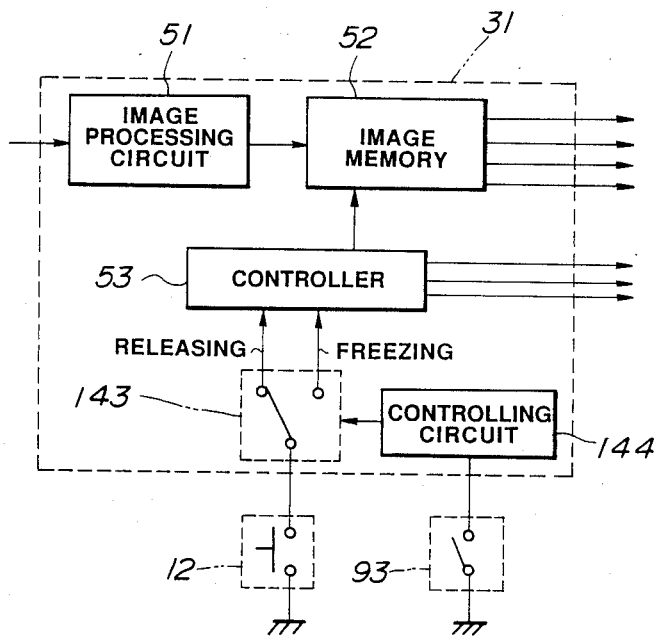

The video circuit 31 in this embodiment is formed as shown in FIG. 26. That is to say, the video circuit 31 comprises an image processing circuit 51 inputting an image signal from a CMR amplifier 20 and making it a video signal, an image memory 52 memorizing the video signal from this image processing circuit 51, a controller 53 transmitting control signal to the above mentioned image memory 52, color image recorder 141, VTR 55 and electronic file 142, a switching switch 143 of one input and two outputs connected to the second operating button 12 and controller 53 and a controlling circuit 144 connected to the releasing and freezing switching switch 93 and controlling the switching of the above mentioned switching switch 143. The above mentioned image memory 52 is controlled in writing in and reading out by the control signal from the above mentioned controller 53. The video signal read out of this image memory 52 is transmitted to the color image recorder 141, VTR 55, electronic file 142 and monitoring apparatus 33. The above mentioned controller 53 will inhibit writing into the image memory 52 and will freeze the image when a freezing signal is input but will transmit a recording instruction to the color image recorder 141 and electronic file 142 when a releasing signal is input. The second operating button 12 is connected to the input end of the above mentioned switching switch 143 whose respective output ends are connected respectively to the releasing signal input end and freezing signal input end of the controller 53.

The other formations are the same as in the first embodiment.

As shown in FIG. 23, the same as in the first embodiment, the operator holds the holding part 8, with the middle finger 37b, third finger 37c and little finger 37d of the left hand, places the thumb 37e on the finger rest 22 of the angle lever 21, places the forefinger 37a on the first operating button 11 highest in the using frequency and, as requried, moves the forefinger 37a to operate the second operating button 12.

In the case of using the second operating button 12 as a freezing switch, the releasing and freezing switch 93 is switched to the freezing side with the right hand so that the controlling circuit 144 may switch the switching switch 143 to the freezing side. In this state, the signal in case the second operating button 12 is pressed will be input into the controller 53 as a freezing signal so that the endoscope image displayed in the monitoring apparatus 33 may be made a still picture.

On the other hand, in the case of using the second operating button 12 as a releasing switch, the releasing and freezing switching switch 93 is switched to the releasing side with the right hand so that the controlling circuit 144 may switch the switching switch 143 to the releasing side. In this state, the signal in case the second operating button 12 is pressed will be input into the controller 53 as a releasing signal so that a still picture may be recorded by the color image recorder 141 and electronic file 142.

The other operations and effects are the same as in the first embodiment.

By the way, in this embodiment, the releasing and freezing switching switch 93 switches only releasing and freezing. However, for example, the second operating button 12 may be made to perform not only the functions of instructing freezing and releasing but also the function of instructing switching the VTR 55 on/off and a switching switch switching thus three functions of this second operating button 12 may be provided so that the second operating button 12 may perform the three functions and the operating part 3 may be made smaller and lighter.

Also, in FIG. 26, the switching switch 143 may be made a releasing and freezing switching switch and the controlling circuit 144 and switch 93 may be omitted.

In FIG. 28 is shown the first modification of the fifth embodiment.

In this modification, a releasing and freezing switching button 100 by a push-button switch is provided instead of the releasing and freezing switching switch 93 of the fifth embodiment. Whether the mode selected by this button 100, that is, the function of the second operating button 12 instructs releasing or freezing is displayed on the picture of the monitoring apparatus 33.

The above mentioned releasing and freezing switching button 100 as a function switching means is provided on the upper surface of the head 92 provided on the side opposite the insertable part of the switching part 9 and is connected to the video circuit 31 through a signal line 99. The above mentioned video circuit 31 outputs a message, for example, of a "releasing mode" or "freezing mode" as superimposed on a video signal by an on-signal from the above mentioned button 100. Therefore, in the monitoring apparatus 33, a message of a "releasing mode" or "freezing mode" will be displayed together with the endoscope image.

The other formations are the same as in the fifth embodiment.

In this modification, in the case of making the endoscope image a still picture, the message displayed on the picture of the monitoring apparatus 33 will be seen. If the message is of a "releasing mode", the releasing and freezing switching button 100 will be pushed with the right hand to change it to be of a "freezing mode" but, if the message is of a "freezing mode", it will be left as it is.

In case the button 100 is pushed, it will output an on-signal to the video circuit 31. In this video circuit 31, the mode will be made a freezing mode by the on-signal and then a message of the "freezing mode" as superimposed on a video signal will be output to the monitoring apparatus 33 and will be displayed. When the operator pushes the second operating button 12, an on-signal will be input into the video circuit 31 through the signal line 98 and, in the video circuit 31, as the freezing mode is already set, this on-signal will be received as a freezing signal and the video signal as a still picture will be output to the monitoring apparatus 33.

Then, in the case of recording the picture, when the button 100 is pushed to set the video circuit 31 in the releasing mode, the message of the monitoring apparatus 33 will be displayed as a "releasing mode".

Then, if the second operating button 12 is pushed, the video circuit 31 will output a releasing signal to the color image recorder 141 and electronic file 142 to record the image.

In this modification, as the mode selected by the releasing and freezing switching button 100 is displayed on the picture of the monitoring apparatus 33, the operator can know immediately the selected mode and the operability can be improved.

The other formations, operations and effects are the same as in the fifth embodiment.

In FIG. 29 is shown the second modification of the fifth embodiment.

In this modification, the releasing and freezing switching switch 93 described in the fifth embodiment is provided on the finger rest 22 side peripheral wall of the head 92.

The other formations are the same as in the fifth embodiment.

In this modification, the releasing and freezing switching switch 93 can be operated with the thumb 37e placed on the finger rest 22.

The releasing and freezing switching switch 93 is thus arranged on the finger rest 22 side and therefore can be operated with the thum 37e of the left hand without using the right hand and all the buttons can be operated with only the left hand. Therefore, the operatability can be further improved.

The other operations and effects are the same as in the fifth embodiment.

Figure 30:
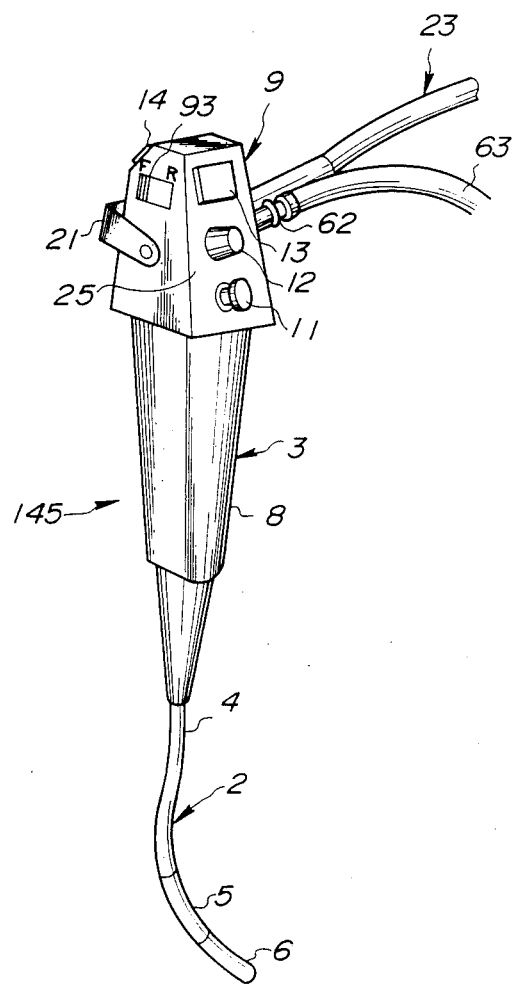
FIG. 30 is a perspective view showing an operating part of an endoscope in the third modification of the fifth embodiment.

In FIG. 30 is shown the third modification of the fifth embodiment.

In this modification, in the endoscope 145 having the first to fourth operating buttons 11 to 14 arranged the same as in the second embodiment shown in FIG. 15, the function of the first operating button 11 is to control suction, the function of the second operating button 12 is to instruct releasing and freezing, the function of the third operating button 13 is to switch the VTR 550 on/off and the function of fouth operating button 14 is to magnify the image or switch the light amount. On the side wall of the switching part 9 is provided a releasing and freezing switching switch 93 for switching the function of the above mentioned second operating button 12.

By the way, instead of providing the above mentioned releasing and freezing switching switch 93, the third operating button 13 or fourth operating button 14 may have a function of switching the function of the second operating button 12.

The other formations, operations and effects are the same as in the second embodiment or fifth embodiment.

In FIGS. 31 to 35 is shown the sixth embodiment of the present invention.

The shape of the switching part 9 of the endoscope 151 of this embodiment is similar to that of the endoscope 91 in the fifth embodiment. That is to say, the switching part 9 is formed to be substantially like a sphere which is incised on the sides to form planes 94 and 95 opposed to each other and substantially parallel with the lengthwise direction of the insertable part 2. On one plane 94 is provided a curving knob 21 and out of the other plane 21 are extended such universal cord 23 and sucking mouthpiece 62 as are shown in FIG. 31.

Figure 31:
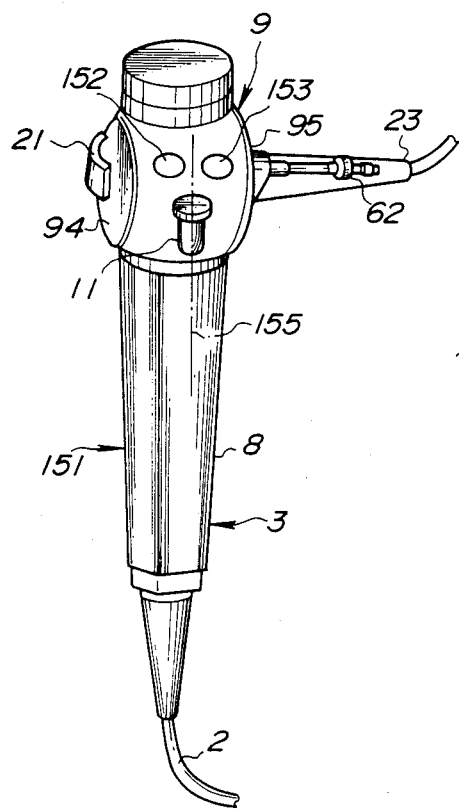
Figure 32:
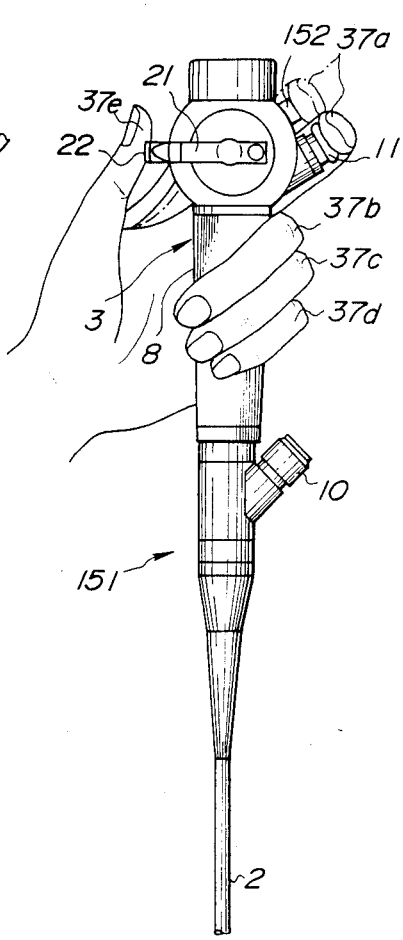

As shown in FIG. 31, the above mentioned switching part 9 is provided with three operating buttons 11, 152 and 153. The first operating button 11 is arranged in the position nearest to the holding part 8 among the three operating buttons. The second operating button 152 and third operating button 153 are arranged in the positions farther from the holding part 8 than this first operating button 11, are in the direction substantially at right angles with the lengthwise direction of the operating part 3 (also of the insertable part 2) and are respectively on the left and right sides.

In this embodiment, the first operating button 11 has a function of controlling suction, the second operating button 152 has a function of instructing releasing and the third operating button 153 has a function of instructing freezing. By the way, the second operating button 152 may have the freezing instructing function, the third operating button 153 may have the releasing instructing function and both operating buttons 152 and 153 may have the same function.

Figure 33:
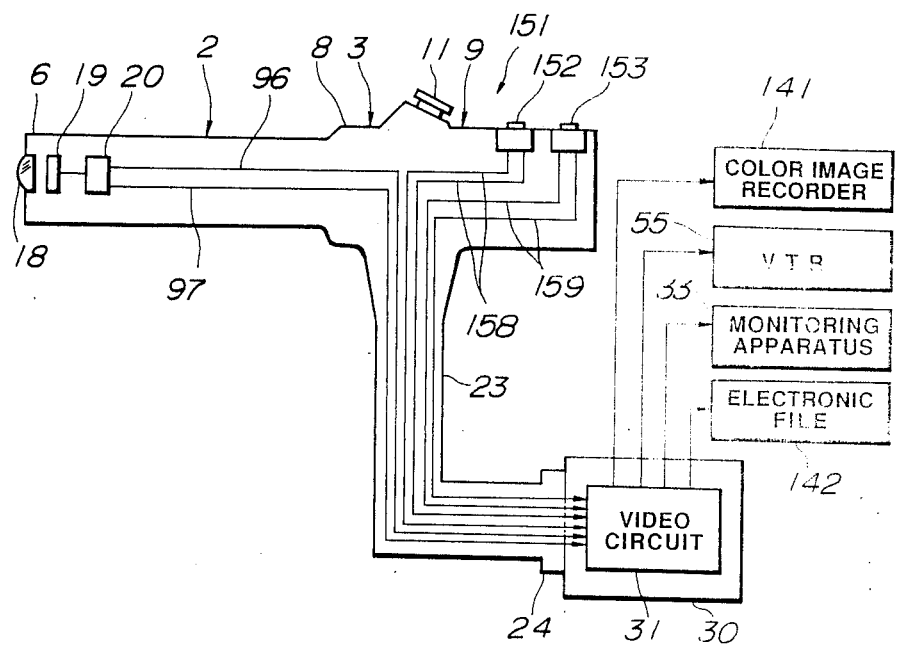

As shown in FIG. 33, the endoscope 151 is connected to a controlling apparatus 30 having a video circuit 31 by a connector 24 provided at the end of a universal cord 23. The above mentioned second operating button 152 and third operating button 153 are connected to the above mentioned video circuit 31 respectively through signal lines 158 and 159. By the way, though not illustrated in FIG. 33, the light source part 32 within the controlling apparatus 30, the light guide 17, sucking tube paths 26 and 28 and suction swithcing valve 27 within the endoscope 91 and the sucking apparatus 39 connected to the above mentioned sucking tube path 28 are the same as in the first embodiment.

A color image recorder 141, VTR 55 and electronic file 142 as of a recording apparatus and a monitoring appartus 33 are connected to the above mentioned controlling apparatus 30.

Figure 34:
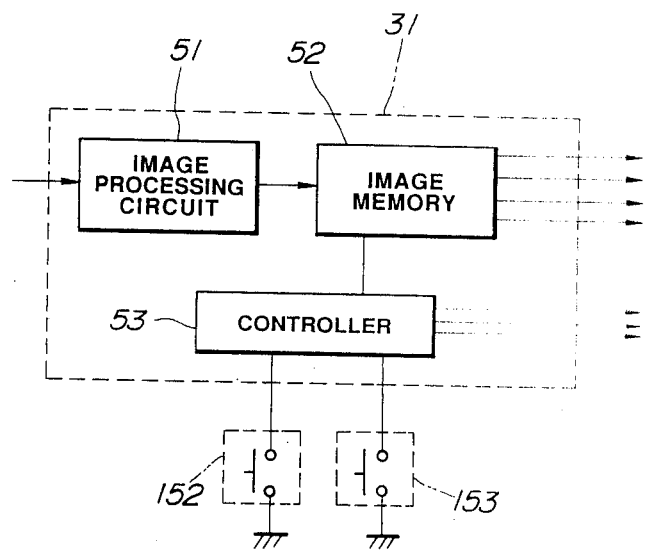

The video circuit 31 in this embodiment is formed as shown in FIG. 34. That is to say, the video circuit 31 is provided with an image processing circuit 51 inputting an image signal from a CMR amplifier 20 and making it a video signal, an image memory 52 memorizing the video signal from this image memory 52 and a controller 53 transmitting control signals to the above mentioned image memory 52, color image recorder 141, VTR 55 and electronic file 142. The second operating button 152 and third operating button 153 are connected to the above mentioned controler 53 so that the releasing signal from the second operating button 152 and freezing signal from the third operating button 153 may be input. The same as in the fifth embodiment, the video signal read out of the image memory 52 within the video circuit 31 is transmitted to the color image recorder 141, VTR 55, electronic file 142 and monitoring apparatus 33. The controller 53 will inhibit writing into the image memory 52 and will freeze the image if a freezing signal is input but will transmit an instruction to record a still picture to the color image recorder 141 and electronic file 142 if a releasing signal is input.

The other formations are the same as in the first embodiment or fifth embodiment.

The operation of this embodiment shall be explained in the following.

Figure 35A:
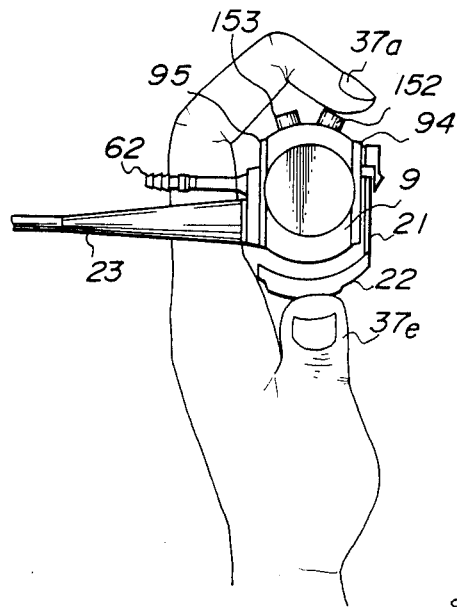
FIG. 35(A) is an explanatory view showing the operating state of a second operating button.
Figure 35B:
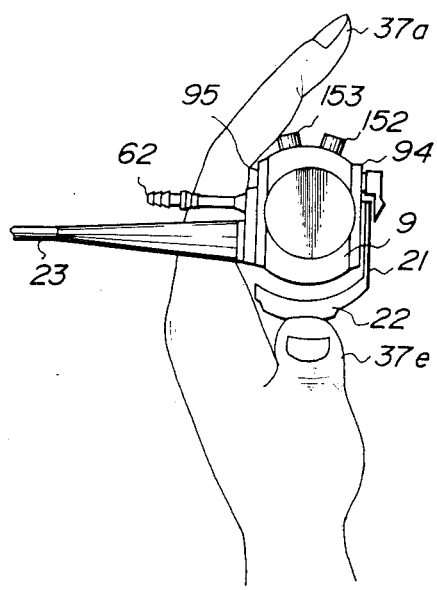
FIG. 35(B) is an explanatory view showing the operating state of a third operating button.
Figure 35C:
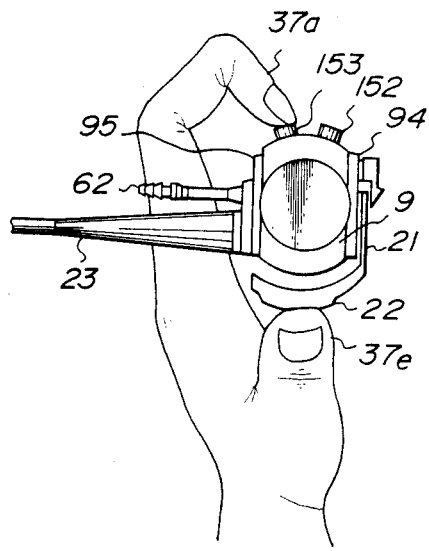
FIG. 35(C) is an explanatory view showing the operating state by another operating method of the third operating button.

The operator usually places the forefinger 37a on the first operating button 11 high in the using frequency. In the case of releasing or freezing, he will place the forefinger 37a on the second operating button 152 which is a releasing switch or on the third operating button 153 which is a freezing switch so as to open the angle between the forefinger 37a and middle finger 37b. In the case of operating the second operating button 152, as shown in FIG. 35(A), the second operating button 152 will be pushed with the tip of the forefinger 37a. In the case of operating the third operating button 153, as shown in FIG. 35(B), it will be pushed with the web near the second joint of the forefinger 37a or, as shown in FIG. 35(C), it will be pushed with the tip of the forefinger 37a by pulling the forefinger 37a to the fitting root side.

In this embodiment, in the case of moving the forefinger 37a from the first operating button 11 to the second or third operating button 152 or 153, the angle between the forefinger 37a and middle finger 37b will be opened but the opened angle between the forefinger 37a and middle finger 37b may be smaller than in the case that the three operating buttons 11, 152 and 153 are provided in the lengthwise direction of the operating part 3 and therefore the operating buttons are easy to operate.

In FIG. 36 is shown the first modification of the third embodiment.

In this modification, the second operating button 152 and third operating button 153 are provided somewhat obliquely to the direction intersecting at right angles with the lengthwsie direction 155 of the operating part 3. In this case, the third operating button 153 is nearer to the holding part 8 than the second operating button 152.

When the forefinger 37a is separated from the middle finger 37b with the third joint (fitting root) as a center to operate the second or third operating button 152 or 153, the forefinger will become a little oblique. In this embodiment, the second and third operating buttons 152 and 153 are arranged in conformity with the angle of the forefinger 37a in this state.

As the second and third operating buttons 152 and 153 are thus arranged, the opening angle between the forefinger 37a and middle finger 37b will be smaller, the operation will be easier and the second and third operating buttons 152 and 153 will be able to be more easily pushed.

In FIG. 37 is shown the second modification of the sixth embodiment.

In this modification, the second operating button 152 arranged farther from the hand holding the holding part 8 is made higher than the third operating button 153 near to the hand so that the difficulty of the forefinger 37a to reach the second operating button 152 will be corrected. By the way, in this modification, the second and third operating buttons 152 and 153 may be arranged as in either of FIGS. 31 and 36.

Figure 38:
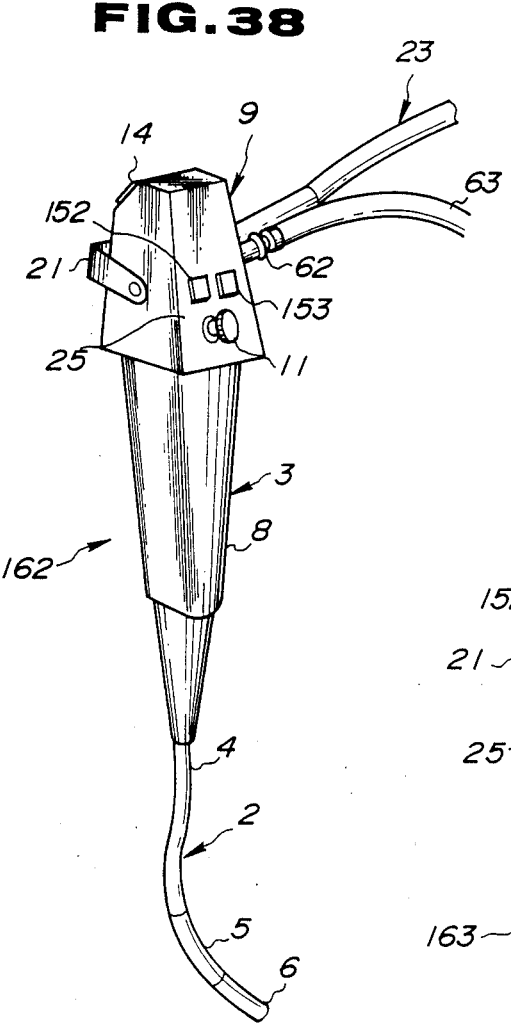
FIG. 38 is a perspective view showing an operating part of an endoscope in the third modification of the sixth embodiment.

In FIG. 38 is shown the third modification of the sixth embodiment.

In this modification, in an endoscope 162 having a switching part 9 of the same shape as in the second embodiment shown in FIG. 15, on the wall surface 25 which is a slope, the first, second and third operating buttons 11, 152 and 153 are arranged the same as in the sixth embodiment shown in FIG. 31.

Figure 39:
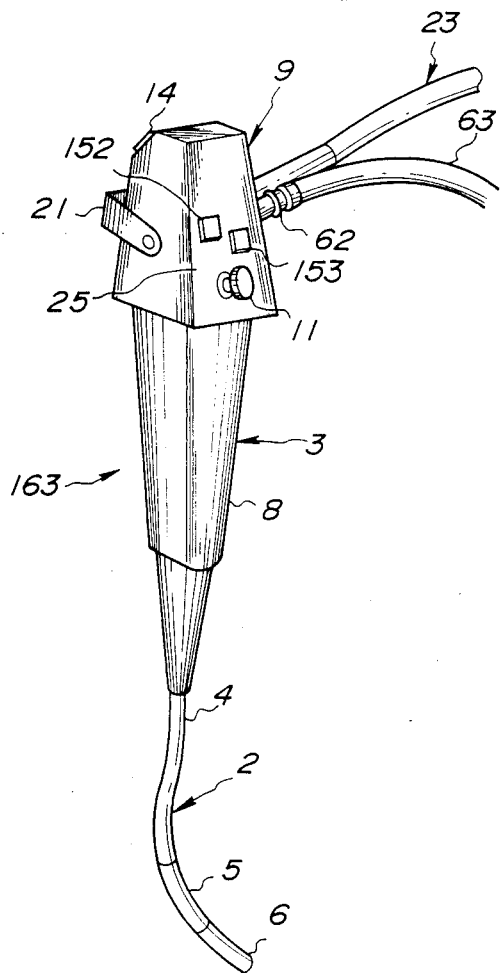
FIG. 39 is a perspective view showing an operating part of an endoscope in the fourth modification of the sixth embodiment.

In FIG. 39 is shown the fourth modification of the sixth embodiment.

In this modification, in the endoscope 162 having the switching part 9 of the same shape as in the second embodiment shown in FIG. 15, on the wall surface 25 which is a slope, the first, second and third operating buttons 11, 152 and 153 are arranged the same as in the first modification of the sixth embodiment.

Figure 40:
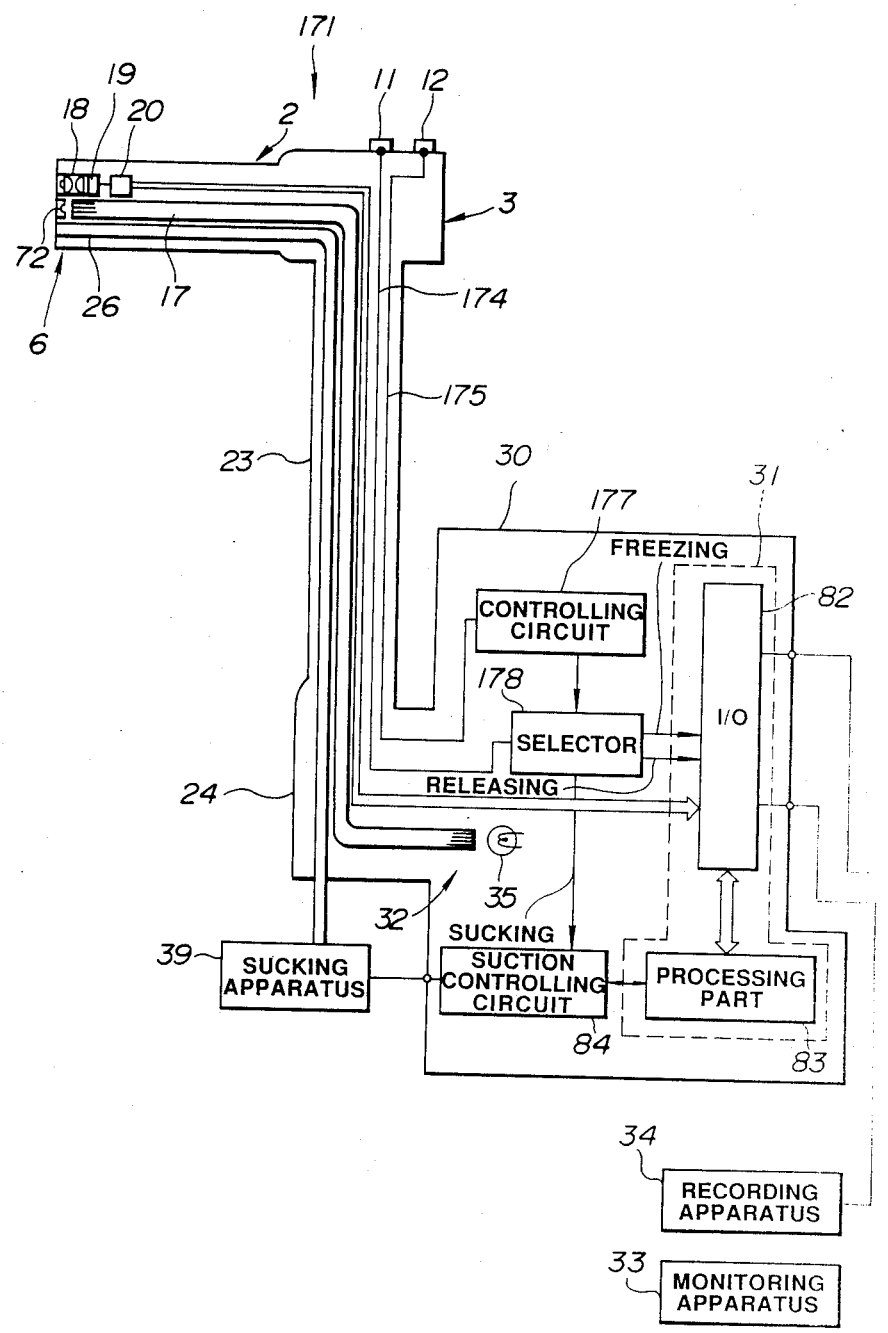
FIG. 40 is a block diagram showing the formation of an endoscope apparatus in the seventh embodiment of the present invention.

In FIG. 40 is shown the seventh embodiment of the prsent invention.

The appearance of an endoscope 171 in this embodiment is the same in the first embodiment shown in FIG. 1.

In this embodiment, the sucking tube path 26 inserted through the insertable part 2 is extended to a connector 24 without the suction switching valve 27 interposed in the cource and is connected to the outside sucking apparatus 39 through this connector 24.

Also, in this embodiment, the first operating button 11 and second operating button 12 are both non-locked type push-button switches of one action.

On the other hand, the controlling apparatus 30 comprises a video circuit 31, light source part 32, controlling circuit 177, suction controlling circuit 84 and selector 178 of one input and three outputs.

The first operating button 11 of the above mentioned endoscope 171 is connected to the input end of the above mentioned selector 178 through a signal line 174. Two of the three output ends of this selector 178 are connected to the freezing signal input end and releasing signal input end of an I/O circuit 82 within the video circuit 30 and the remaining one is connected to a suction controlling circuit 84 which is connected to the above mentioned suction controlling apparatus 39 to control it. The second operating button 12 is connected through a signal line 175 to the above mentioned controlling circuit 177 which transmits a switching signal to the above mentioned selector 178 in response to the operation of the above mentioned second operating button 12. That is to say, when the second operating button 12 is pushed, the controlling circuit 177 will output a switching signal to the selector 178 and, in response to this switching signal, the selector 178 will switch and connect its input end to the freezing signal input end side and releasing signal input end side of the I/O circuitr 82 and the suction controlling circuit 84 side in turn. Therefore, when the second operating button 12 is operated, the function of the first operating button 11 will be switched in the order, for example, of instructing freezing → instructing releasing → controlling sucking → instructing freezing ... The apparatus or operation operated by operating the above mentioned first operating button 11 is to be displayed in the monitoring apparatus 33.

By the way, the formation of the above mentioned video circuit 31 is the same as is shown in FIG. 21.

Therefore, in case the signal line 174 of the first operating button 11 is connected to the freezing signal input end of the I/O circuit 82 of the video circuit 31 by operating the second operating button 12, by operating the first operating button 11, the image displayed in the monitoring apparatus will be made a still picture by the video circuit 31. Also, in case the signal line 174 of the first operating button 11 is connected to the releasing signal input end of the above mentioned I/O circuit 82 by operating the second operating button 12, by operating the first operating button 11, the image displayed in the monitoring apparatus 33 will be recorded in such recording medium as a disc cartridge by the video circuit 31. Further, in case the signal line 174 of the first operating button 11 is connected to the controlling end of the suction controlling circuit 84 by operating the second operating button 12, by operating the first operating button 11, the sucking apparatus 39 will suck a body liquid or the like within the body cavity by the signal from the sucking controlling circuit 84. By the way, the recording apparatus 34 may be an optical information recording apparatus 34 may be an optical information recording apparatus using a photomagnetic disc or the like as a recording medium or a still camera using a film as recording medium.

The other formations, operations and effects are the same as in the first embodiment.

By the way, the present invention is not limited to the above mentioned various embodiments and can be applied not only to the endoscope for bronchial tubes but also to other endoscopes required particularly, for example, to be small and light.

Also, the present invention can be applied to an optical endoscope having an eyepiece part at the rear end of the operating part and having within the insertable part an image guide transmitting to the above mentioned eyepiece part an object image formed by an objective lens system. In such case, the optical endoscope may be provided in the switching part of the operating part with a switch having a function of instructing freezing and releasing so that, in case a television camera is connected to the eyepiece part of this endoscope, the above mentioned switch and television camera may be connected with each other through a contact or the like provided in the eyepiece part and the above mentioned switch may perform the function of instructing freezing and releasing. Also, in the case of the above mentioned optical endoscope, the functions of the switch provided in the switching part may be of not only controlling sucking but also instructing releasing, switching the light amount and controlling feeding air and water.

Also, the switching part may be provided with a plurality of switches each performing a plurality of functions.

It is apparent that, in this invention, working modes different in a wide range can be formed on the basis of this invention without deviating from the spirit and scope of the invention. This invention is not restricted by its specific working mode except being limited by the appended claims.

What is claimed is:

1. An endoscope comprising:
   an elongate insertable part including an observing window in the tip part and a sucking tube path in the interior;
   an image forming optical system for receiving a light from an object coming in from said observing window and forming an endoscope image;
   an imaging means for imaging said endoscope image formed by said image forming optical system;
   an operating part connected to said insertable part at the base on the side opposite said tip part and including a holding part arranged on the side near to said insertable part and a switching part arranged on the side far from said insertable part;
   said switching part including a plurality of switching means, said plurality of switching means including a first switching means arranged in the position nearest to said holding part among said plurality of switching means and a second switching means arranged in the position farther from said holding part than said first switching means and said first switching means including a function of controlling sucking using said sucking tube path.

2. An endoscope according to claim 1 wherein said first switching means is arranged just near to the end on said holding part side of said switching part, said second switching means is arranged in a position distinguishable in the operation from said first switching means and near to said first switching means and said first switching means and second switching means are arranged substantially in the lengthwise direction of said insertable part.

3. An endoscope according to claim 1 wherein said first switching means and second switching means are arranged so closely to each other as to be selectively operated with the forefinger of the hand holding said holding part.

4. An endoscope according to claim 3 further comprising a curving means including a curvable part provided in said insertable part and a curving operating means provided in said operating part and for curving said curvable part, said curving opetating means including an operating member arranged on the surface side opposite the plane including said plurality of switching means of said switching part so as to be operatable with the thumb of the hand holding said holding part.

5. An endoscope according to claim 1 further comprising a connecting means for connecting said operating part and outside apparatus with each other and a sucking mouthpiece communicating with said sucking tube path, said connecting means at said operating part side end and said sucking mouthpiece being arranged on the left side surface in case the plane including said plurality of switching means is made a front surface in said switching part and said first switching means and said second switching means being arranged on said insertable part side more than an imaginary plane including the respective center axes of said connecting means and sucking mouth piece.

6. An endoscope according to claim 3 wherein said first switching means and second switching means are both push-button switches and both said switching means pushing directions are parallel with each other.

7. An endoscope according to claim 6 wherein said first switching switch and second switching switch are provided on the same surface which is substantially a plane.

8. An endoscope according to claim 1 wherein said second switching means includes a function of instructing recording a still picture of said endoscope image.

9. An endoscope according to claim 1 wherein said second switching means includes a function of instructing making said endoscope image a still picture.

10. An endoscope according to claim 1 wherein said first switching means and second switching means are both push-button switches.

11. An endoscope according to claim 1 wherein said second switching means includes a plurality of functions.

12. An endoscope according to claim 11 wherein said plurality of functions include a function of instructing recording a still picture of said endoscope image and a function of instructing making said endoscope image a still picture.

13. An endoscope according to claim 11 wherein said second switching means is a push-button switch of twp steps performing two functions.

14. An endoscope according to claim 13 wherein the first step of said push-button switch performs said function of instructing making a still picture and the second step performs said function of instructing recording a still picture.

15. An endoscope according to claim 11 wherein said second switching means performs said plurality of functions by a plurality of operating patterns and said endoscope is further provided with a judging means for judging said plurality of operating patterns of said second switching means.

16. An endoscope according to claim 11 further comprising a means for switching the function of said second switching means.

17. An endoscope according to claim 1 wherein said first switching means has a plurality of functions including said function of controlling sucking.

18. An endoscope according to claim 17 wherein one of said plurality of functions is a function of instructing making said endoscope image a still picture.

19. An endoscope according to claim 18 wherein said first switching means is a push-button switch of two steps performing two functions.

20. An endoscope according to claim 19 wherein the first step of said push-button switch performs said function of instructing making a still picture and the second step performs said function of controlling sucking.

21. An endoscope according to claim 17 wherein one of said plurality of functions is a function of instructing recording a still picture of said endoscope image.

22. An endoscope according to claim 21 wherein said second switching means includes a function of instructing making said endoscope image a still picture and said first switching means has the function switched by said second switching means so as to perform said function of instructing recording a still picture in the state that it is instructed to make a still picture by said second switching means and to perform said function of controlling sucking in other states.

23. An endoscope comprising:
an elongate insertable part including an observing window in the tip part and a sucking tube path in the interior;
an image forming optical system for receiving a light from an object coming in from said observing window and formiong an endoscope image;
an imaging means for imaging said endoscope image formed by said image forming optical system;
an operating part connected to said insertable part at the base on the side opposite said tip part and including a holding part arranged on the side near to said insertable part and a switching part arranged on the side far from said insertable part;
said switching part including a plurality of swithcing means, said plurality of switching means including a first switching means arranged in the position nearest to said holding part among said plurality of switching means and a second switching means the third switching means arranged in the positions farther from said holding part than said first switching means, said first switching means including a function of controlling sucking using said sucking tube path and said second switching means and third switching means being arranged in the direction intersecting substantially at right angles with the lenthwise direction of said operating part.

24. An endoscope according to claim 23 wherein one of said second switching means and third switching means has a function of instructing making said endoscope image a still picture and the other has a function of instructing recording a still picture of said endoscope image.

25. An endoscope apparatus comprising:
an endoscope body having an elongate insertable part including an observing window in the tip part and a sucking tube path in the interior, an image forming optical system for receiving a light from an object coming in from said observing window and forming an endoscope image and an operating part connected to said insertable part at the base on the side opposite said tip part and including a holding part arranged on the side near to said insertable part and a switching part arranged on the side far from said insertable part;
an imaging means for imaging said endoscope image formed by said image forming optical system;
a signal processing means for making the signal from said imaging means an image signal;
a means for making the image made the image signal by said signal processing means a still picture;
a recording means for recording an image by inputting the signal from said signal processing means;
a sucking means connected to said sucking tube path and for sucking using said sucking tube path;
said switching part having a plurality of switching means for performing a plurality of functions including a function of controlling said sucking using said sucking tube path, a function of instructing said recording means to record said image and a function of instructing said means for making still picture to make a still picture and the switching means arranged in the position nearest to said holding part among said plurality of switching means including said function of controlling sucking.

26. An endoscope comprising:
an elongate insertable part including an observing window in the tip part and a sucking tube path in the interior;
an observing means for obtaining an endoscope image including an image forming optical system for receiving a light from an object coming in from said observing window and forming an endoscope image;
an operating part connected to said insertable part at the base on the side opposite said tip part and including a holding part arranged on the side near to said insertable part and a switching part arranged on the side far from said insertable part;
said switching part including a plurality of switching means and the switching means arranged in the position nearest to said holding part among said plurality of switching means including a function of controlling sucking using said sucking tube path.

* * * * *